(12) United States Patent
Jones et al.

(10) Patent No.: US 11,352,598 B2
(45) Date of Patent: Jun. 7, 2022

(54) FLUID MIXING SYSTEMS INCLUDING HELICAL MIXING ASSEMBLY WITH IMPELLER ATTACHMENT AND METHODS OF USE

(71) Applicant: LIFE TECHNOLOGIES CORPORATION, Carlsbad, CA (US)

(72) Inventors: Nephi Jones, Newton, UT (US); Steven Kjar, Logan, UT (US); Brycen Mills, Nibley, UT (US); Mark Smith, Nibley, UT (US); Derik West, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 575 days.

(21) Appl. No.: 16/238,618

(22) Filed: Jan. 3, 2019

(65) Prior Publication Data

US 2019/0217261 A1 Jul. 18, 2019

Related U.S. Application Data

(60) Provisional application No. 62/712,343, filed on Jul. 31, 2018, provisional application No. 62/670,934, (Continued)

(51) Int. Cl.
*B22C 5/00* (2006.01)
*C12M 1/42* (2006.01)
(Continued)

(52) U.S. Cl.
CPC .......... *C12M 35/04* (2013.01); *B01F 23/233* (2022.01); *B01F 27/054* (2022.01); (Continued)

(58) Field of Classification Search
CPC .................................................. C12N 5/0602
See application file for complete search history.

(56) References Cited

U.S. PATENT DOCUMENTS

| 659,345 A | 10/1900 | Ivins |
| 1,711,114 A | 4/1929 | Hunt |

(Continued)

FOREIGN PATENT DOCUMENTS

| CN | 101163538 A | 4/2008 |
| CN | 202606066 U | 12/2012 |

(Continued)

OTHER PUBLICATIONS

ATMI Life Sciences, *Integrity PadReadtor, A New Culture in Cell Growth*, published as early as 2010, 4 pages.

(Continued)

*Primary Examiner* — Anshu Bhatia
*Assistant Examiner* — Gregory Y Huan
(74) *Attorney, Agent, or Firm* — Workman Nydegger

(57) ABSTRACT

The present set of embodiments relate to a bioproduction system, method, and apparatus for mixing a fluid. The bioproduction mixing system includes an offset helical assembly having a stabilizer and impeller for mixing a fluid within a flexible compartment The bioproduction mixing system is designed for efficient mixing of the fluid and for use with a variety of different impellers that can be located at different locations according to the volume and shape characteristics of the flexible compartment. The bioproduction mixing system is optimized to eliminate stagnation zones while maximizing bulk fluid flow.

20 Claims, 35 Drawing Sheets

Related U.S. Application Data filed on May 14, 2018, provisional application No. 62/618,215, filed on Jan. 17, 2018.

(51) Int. Cl.

| | | |
|---|---|---|
| *C12M 1/00* | (2006.01) | |
| *C12N 5/071* | (2010.01) | |
| *C12M 1/06* | (2006.01) | |
| *B01F 23/233* | (2022.01) | |
| *B01F 27/054* | (2022.01) | |
| *B01F 27/92* | (2022.01) | |
| *B01F 27/114* | (2022.01) | |
| *B01F 27/213* | (2022.01) | |
| *B01F 35/43* | (2022.01) | |
| *B01F 35/513* | (2022.01) | |
| *B01F 35/32* | (2022.01) | |
| *B01F 35/41* | (2022.01) | |
| *C12M 1/36* | (2006.01) | |
| *B01F 27/90* | (2022.01) | |
| *B01F 35/30* | (2022.01) | |
| *B01F 101/44* | (2022.01) | |

(52) U.S. Cl.
CPC .......... *B01F 27/114* (2022.01); *B01F 27/213* (2022.01); *B01F 27/92* (2022.01); *B01F 35/3204* (2022.01); *B01F 35/4121* (2022.01); *B01F 35/43* (2022.01); *B01F 35/513* (2022.01); *C12M 23/50* (2013.01); *C12M 23/58* (2013.01); *C12M 27/02* (2013.01); *C12M 27/06* (2013.01); *C12M 41/48* (2013.01); *C12N 5/0602* (2013.01); *B01F 23/23362* (2022.01); *B01F 27/90* (2022.01); *B01F 35/3214* (2022.01); *B01F 2035/352* (2022.01); *B01F 2101/44* (2022.01); *C12N 2527/00* (2013.01)

(56) References Cited

U.S. PATENT DOCUMENTS

| | | | |
|---|---|---|---|
| 1,752,833 A | | 4/1930 | Brumder |
| 1,778,188 A | | 10/1930 | Guy |
| 1,898,724 A | | 2/1933 | Gifford |
| 1,954,093 A | | 4/1934 | Nelson |
| 2,552,057 A | | 5/1951 | Paik |
| 2,896,926 A | | 7/1959 | Chapman |
| 3,281,124 A | * | 10/1966 | Bartl ............... B01J 19/18 366/325.94 |
| 3,322,401 A | | 5/1967 | Mersch |
| 3,559,962 A | | 2/1971 | Enssle et al. |
| 3,692,427 A | | 9/1972 | Risse |
| 4,083,653 A | | 4/1978 | Stiffler |
| 4,355,906 A | | 10/1982 | Ono |
| D273,709 S | | 5/1984 | Schneider |
| 4,712,922 A | * | 12/1987 | Feterl ................ A01K 5/002 366/288 |
| 4,722,608 A | | 2/1988 | Salzman et al. |
| D336,034 S | | 6/1993 | Rebilas |
| 5,411,331 A | | 5/1995 | Griffin |
| 5,454,797 A | | 10/1995 | Haswell |
| 5,885,001 A | | 3/1999 | Thomas |
| 5,896,989 A | | 4/1999 | Ropiak et al. |
| 5,941,636 A | | 8/1999 | Lu |
| 6,083,587 A | | 7/2000 | Smith et al. |
| D439,328 S | | 3/2001 | Nielsen |
| 6,670,171 B2 | | 12/2003 | Carll |
| 6,844,186 B2 | | 1/2005 | Carll |
| 7,229,206 B2 | | 6/2007 | Whitney |
| 7,384,783 B2 | | 6/2008 | Kunas et al. |
| 7,441,940 B2 | | 10/2008 | Vanek |
| 7,487,688 B2 | | 2/2009 | Goodwin |
| 7,682,067 B2 | | 3/2010 | West et al. |
| 7,878,099 B2 | | 2/2011 | Loibl |
| 7,879,599 B2 | | 2/2011 | Goodwin et al. |
| D662,212 S | | 6/2012 | Quisenberry |
| 8,272,410 B2 | | 9/2012 | Elgan et al. |
| 8,342,737 B2 | | 1/2013 | Greller et al. |
| D679,023 S | | 3/2013 | Quisenberry |
| 8,455,242 B2 | | 6/2013 | Staheli et al. |
| 8,506,198 B2 | | 8/2013 | West et al. |
| 8,603,805 B2 | | 12/2013 | Goodwin et al. |
| 8,641,314 B2 | | 2/2014 | Thacker et al. |
| 9,005,971 B2 | | 4/2015 | Jones et al. |
| 9,643,133 B2 | | 5/2017 | Goodwin et al. |
| 9,839,886 B2 | | 12/2017 | Staheli |
| 9,932,553 B2 | | 4/2018 | Jones et al. |
| D824,042 S | | 7/2018 | Scott et al. |
| D830,544 S | | 10/2018 | Kisner et al. |
| D857,188 S | | 8/2019 | Moran et al. |
| D870,315 S | | 12/2019 | Wahlqvist et al. |
| D870,989 S | | 12/2019 | Penland |
| 2002/0105856 A1 | | 8/2002 | Terentiev |
| 2002/0131654 A1 | | 9/2002 | Smith et al. |
| 2003/0077466 A1 | | 4/2003 | Smith et al. |
| 2006/0240546 A1 | | 10/2006 | Goodwin et al. |
| 2006/0270036 A1 | | 11/2006 | Goodwin et al. |
| 2007/0014187 A1 | | 1/2007 | Kaas |
| 2010/0165785 A1 | | 7/2010 | Kaas |
| 2010/0260010 A1 | | 10/2010 | Jornitz |
| 2011/0013473 A1 | | 1/2011 | Ludwig et al. |
| 2011/0013474 A1 | | 1/2011 | Ludwig et al. |
| 2011/0026360 A1 | | 2/2011 | Greller et al. |
| 2011/0058447 A1 | | 3/2011 | Reif et al. |
| 2011/0058448 A1 | | 3/2011 | Reif et al. |
| 2011/0188928 A1 | | 8/2011 | West et al. |
| 2011/0229963 A1 | | 9/2011 | Fatherazi et al. |
| 2011/0310696 A1 | * | 12/2011 | Goodwin ............ B01F 15/0085 366/204 |
| 2013/0101982 A1 | | 4/2013 | Goodwin et al. |
| 2013/0279289 A1 | | 10/2013 | Eggler et al. |
| 2014/0106453 A1 | | 4/2014 | Kunas et al. |
| 2015/0117142 A1 | | 4/2015 | Staheli et al. |
| 2017/0011714 A1 | | 1/2017 | Eim et al. |
| 2017/0183617 A1 | | 6/2017 | Jones et al. |

FOREIGN PATENT DOCUMENTS

| | | |
|---|---|---|
| DE | 202009005407 U1 | 9/2009 |
| DE | 102008058338 A1 | 5/2010 |
| EP | 1776998 A1 | 4/2007 |
| EP | 2123745 A2 | 11/2009 |
| FR | 782935 | 9/1934 |
| JP | H06285353 A | 10/1994 |
| JP | 2004-532719 A | 10/2004 |
| JP | 2013-544186 A | 12/2013 |
| WO | 2010/089151 A1 | 8/2010 |
| WO | 2011/139209 A1 | 11/2011 |
| WO | 2012/097079 A2 | 7/2012 |
| WO | 2013/151733 A1 | 10/2013 |
| WO | 2015/039034 A1 | 3/2015 |
| WO | 2017/023638 A1 | 2/2017 |
| WO | 2017/064058 A1 | 4/2017 |

OTHER PUBLICATIONS

ATMI Life Sciences, *Integrity PadReadtor, All Applications, High-End Controls and Abilities*, published as early as 2010, 4 pages.

International Search Report and Written Opinion dated Apr. 20, 2017, issued in PCT Application No. PCT/US2016/068064, filed Dec. 21, 2016.

Communication under Rule 71(3) EPC received for European Application No. 16826262.4, dated Sep. 24, 2021, 6 pages.

\* cited by examiner

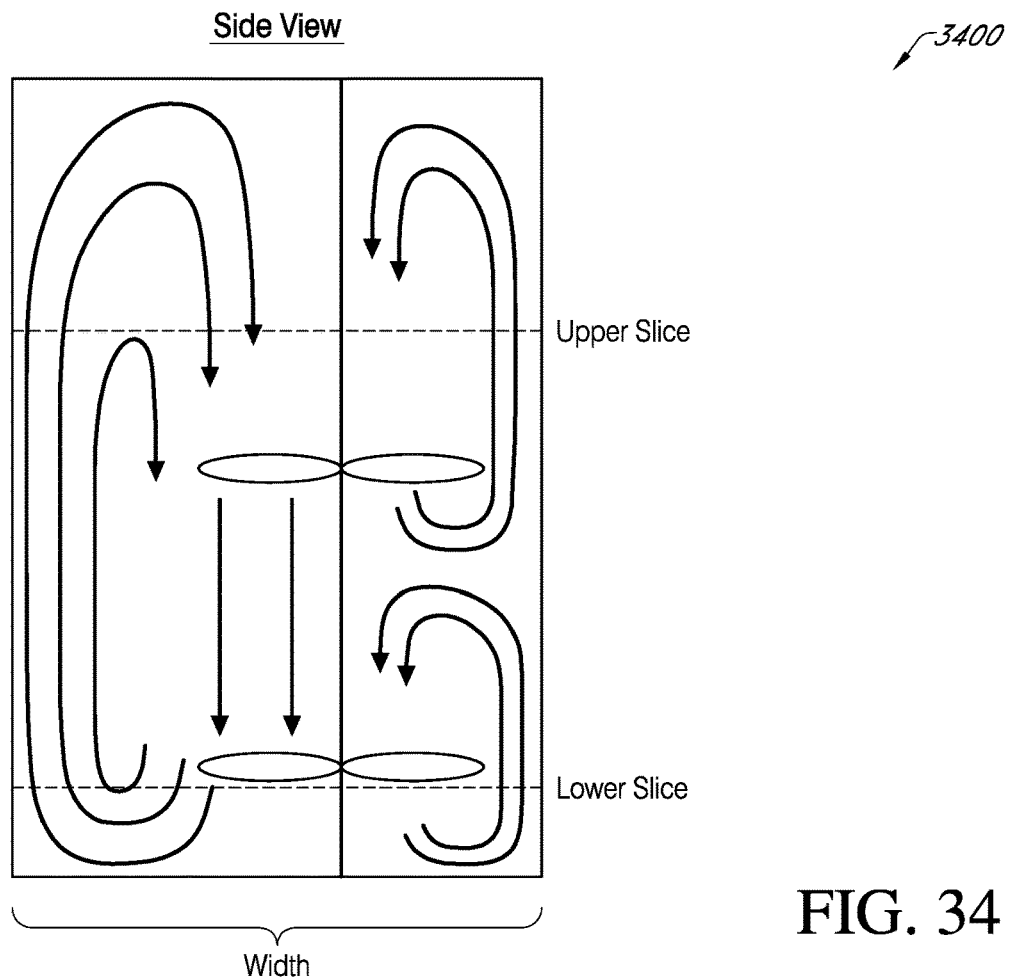
FIG. 34
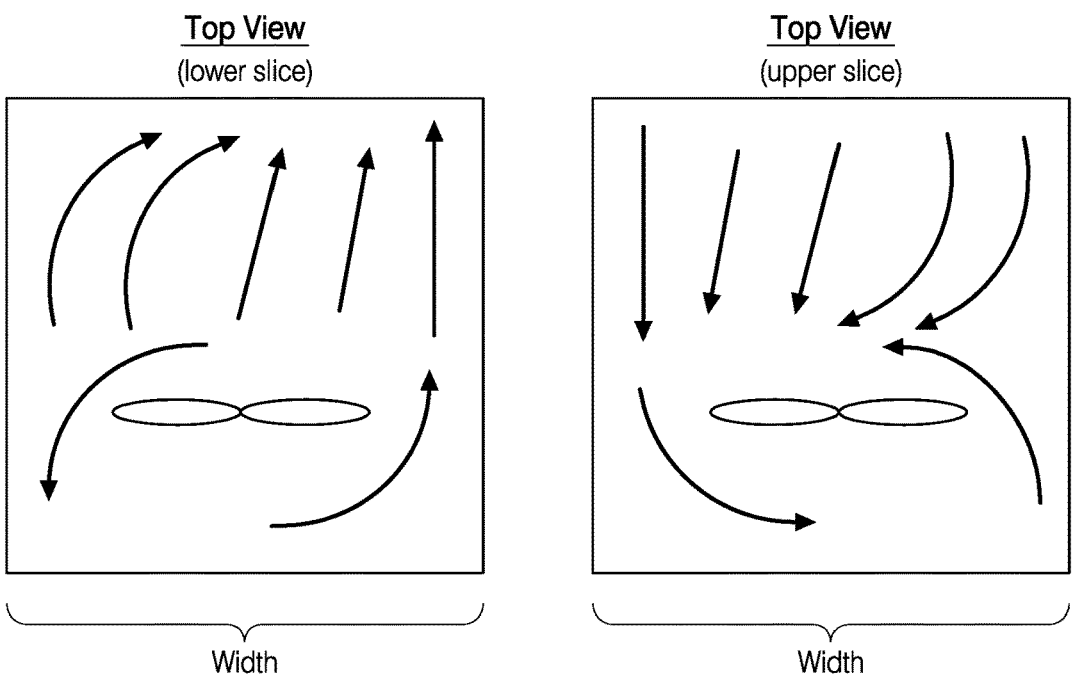

FLUID MIXING SYSTEMS INCLUDING HELICAL MIXING ASSEMBLY WITH IMPELLER ATTACHMENT AND METHODS OF USE

CROSS-REFERENCE TO RELATED APPLICATIONS

This application claims priority to U.S. Provisional Application No. 62/712,343, filed Jul. 31, 2018, U.S. Provisional Application No. 62/670,934, filed May 14, 2018, and U.S. Provisional Application No. 62/618,215, filed on Jan. 17, 2018, which are incorporated herein by specific reference.

BACKGROUND

The biopharmaceutical industry uses a broad range of mixing systems for a variety of processes such as in the preparation of media and buffers and in the growing, mixing and suspension of cells and microorganisms. Some conventional mixing systems, including bioreactors and fermenters, comprise a flexible bag disposed within a rigid support housing. An impeller is disposed within the flexible bag and is coupled with the drive shaft. Rotation of the drive shaft and impeller facilitates mixing and/or suspension of the fluid contained within flexible bag.

Although the current mixing systems are useful, they have some limitations. For example, where the drive shaft is secured within the flexible bag during the manufacturing process, the rigid drive shaft limits the ability to collapse or fold the flexible bag so as to reduce its size for transportation, storage and/or further processing. Likewise, where it is intended to reuse the drive shaft, such as when it is made of metal, this system has the disadvantage of needing to clean and sterilize the drive shaft between different uses.

Currently available disposable mixing systems often have height limitations with regard to mixing efficiency. For example, currently employed magnetic mixings necessarily have a magnetic stir element near the bottom of the vessel because it must be able to magnetically interact with an element outside of the sterile system to provide the electromagnetic force to turn the magnetic stir element. Other systems employ rigid driveshaft systems that must become exponentially thicker due to increased sheer forces acting on the driveshaft as the driveshaft becomes long to accommodate taller mixing vessels.

Additionally, many currently available disposable fluid mixing systems are cylindrical in nature and either require baffles to increase bulk fluid flow or simple suffer from reduced mixing efficiency. Another disadvantage of currently available disposable mixing systems is the ability to create custom vessels sizes based on the limitations listed above.

What is needed is a system that employs a drive mechanism that is capable of accommodating a large variety of vessels sizes and increasing mixing efficiency without the need to complex baffling systems. Such a system would be able to provide mixing forces from any height within a vessel as well as take advantage of an irregular shaped mixing vessel to increase bulk fluid flow.

BRIEF SUMMARY

In one aspect, a bioproduction mixing system is disclosed. The system may include a helical assembly including a first line and a second line, a stabilizer including a first portion and a cross member having a first end and a second end, wherein the first end engages the first line and the second end engages the second line, an impeller including a second portion, a first attachment, and a second attachment, wherein the first attachment engages the first line and the second attachment engages the second line, and the first portion interacts with the second portion to orient the impeller relative to the first and second lines. In some embodiments, the first portion is a stem and the second portion is a tubular receiver configured to accept the stem. In some embodiments, the first and second lines each include a plurality of openings and the first end projects into a first opening on the first line and the second end projects into a first opening on the second line. In some embodiments, the first attachment projects into an opening on the first line and the second attachment projects into an opening on the second line. In some embodiments, stabilizer caps affix to the ends to secure the stabilizer to the first and second lines. In some embodiments, impeller caps affix to the first and second attachments to secure the impeller to the first and second lines. The system may comprise a plurality of rungs, wherein each rung has a first protrusion projecting into an opening on the first line and a second protrusion projecting into an opening on the second line, wherein the protrusions affix to rung caps to secure the rungs to the lines. The system may comprise a flexible container having a first end, a second end, and a sidewall, wherein the first and second lines are each suspended between the first and second ends of the flexible container and the first and second lines are spaced apart and on opposing sides of a driveline axis. In some embodiments, a first bearing assembly is mounted to the first end of the flexible container and a second bearing assembly is mounted to the second end of the flexible container to provide rotational movement to the helical assembly. In some embodiments, the flexible container further comprises an inlet for introducing a fluid into the flexible compartment, an outlet for removing a fluid from the flexible compartment, at least one sensor port for receiving a sensor, and a sparger for introducing a gas into the fluid within the flexible compartment. The system may comprise a rigid housing adapted to receive the flexible container, wherein the rigid housing includes a rigid housing support and a motor configured to engage the first bearing assembly and provide rotational energy to the helical assembly.

In one aspect, a method for manufacturing and operating a bioproduction mixing assembly is disclosed. The method may include providing a helical assembly including a first line and a second line, the first line and the second lines each have a first end and a second end and the first and second lines are spaced apart from one another, connecting a first end of a stabilizer to the first line and a second end of the stabilizer to the second end, and connecting a first attachment of an impeller to the first line and a second attachment of the impeller to the second line. The method may include the step of rotating the helical assembly to mix a fluid within a flexible compartment, wherein the flexible compartment has a first end, a second end, and a sidewall. In some embodiments, rotating the helical assembly causes the first and second lines to wrap about a driveline axis. The method may include the step of moving the stabilizer and impeller from a first position to a second position relative to one another, wherein a stabilizer stem slides within an impeller receiver to facilitate the positional change. The method may include the step maintaining the same impeller orientation between the first and second positions. The method may include the step of spacing the first line and the second line at a helical width from one another by attaching the first ends of the first and seconds lines to a yoke that is adjacent to the first end of the flexible container and attaching the second ends of the first and second lines to an impeller/yoke that is adjacent to the second end of the flexible container. The method may include the step of providing additional spacing support by affixing a first protrusion of a rung to the first line and a second protrusion of the rung to the second line. The method may include the step of attaching the impeller, stabilizer, and rung to the first and second lines by projecting the first and second ends of the stabilizer through a first set of openings in the first and second lines, projecting the first and second attachments through a second set of openings in the first and second lines, and projecting the first and second protrusions through a third set of openings in the first and second lines. The method may include the step of securing the ends, attachments, and protrusions to the first and second lines using caps. The method may include the step of providing low volume mixing within the flexible compartment by rotating the impeller/yoke.

In one aspect, a bioproduction mixing system is disclosed. The system may comprise a compartment, wherein the flexible compartment includes a first end, a second end, and a sidewall, and a helical assembly suspended between the first and second ends of the compartment, wherein the assembly is offset from a center axis spanning the first and second ends of the compartment. In some embodiments, the compartment is flexible and has a rectangular in shape to resist vortex formation and provide a baffling characteristic. In some embodiments, the offset location is on a corner line. In some embodiments, the offset location on a sidewall line. In some embodiments, the offset is about 14% of the total compartment width to optimize bulk flow. In some embodiments, the offset is between 12% and 16% of the total compartment width to optimize bulk flow. In some embodiments, the offset is between 10% and 18% of the total compartment width to optimize bulk flow. In some embodiments, the offset is between 8% and 20% of the total compartment width to optimize bulk flow. In some embodiments, the offset is between 6% and 22% of the total compartment width to optimize bulk flow. In some embodiments, the offset is between 4% and 24% of the total compartment width to optimize bulk flow. In some embodiments, the offset is between 2% and 26% of the total compartment width to optimize bulk flow. The system may include a first bearing assembly mounted to the first end of the compartment, the first bearing assembly including a drive shaft protruding into the compartment and a yoke assembled onto the drive shaft, and a second bearing assembly mounted to the second end of the compartment, the second bearing assembly having a yoke/impeller assembly mounted thereto. In some embodiments, the yoke and yoke/impeller assembly shapes are selected to provide spacing between a first line and a second line of the helical assembly. In some embodiments, the second bearing assembly further includes a thrust pin protruding into the flexible compartment and a pull handle extending outwardly from the flexible compartment, the thrust pin and pull handle physically communicate through a seal port.

In one aspect, a method for increasing mixing efficiency of a bioproduction fluid is disclosed. The method may include positioning a helical drive assembly within a compartment offset to a centerline to optimize a baffling characteristic and optimize bulk fluid flow, wherein the compartment has a first end, a second end, and a sidewall and the helical drive assembly is suspended between the first and second ends and rotating the helical drive assembly to mix a fluid within the flexible compartment. In some embodiments, the compartment is flexible and rectangular in shape.

The method may include the step of installing the compartment into a rigid housing by connecting a driveshaft to a motor, wherein the driveshaft has a first end and a second end, the first end of the driveshaft protrudes from the first end of the compartment to engage the motor and the second end of the driveshaft is sterily positioned within the compartment to provide rotational movement to the helical drive assembly through a first bearing assembly. In some embodiments, the step of installing the compartment further comprises using a pull handle to position the second end of the compartment within the rigid housing. In some embodiments, a yoke is attached to the second end of the driveshaft and is shaped to provide a helical width to a first line and a second line of the helical assembly. In some embodiments, a yoke/impeller assembly is positioned near the second end of the compartment and is shaped to provide a helical width to the first and second lines of the helical assembly. The method may include the step of mixing a low volume using the yoke/impeller assembly. The method may include the step of affixing the first and second lines to the yoke through interaction of a plurality of pegs projecting from the yoke with a plurality of openings in the lines. In some embodiments, a second bearing assembly is positioned on the second end of the flexible compartment to provide rotational movement to the yoke/impeller assembly. In some embodiments, the offset location is on a corner line. In some embodiments, the offset location on a sidewall line. In some embodiments, the offset is about 14% of the total compartment width to optimize bulk flow. In some embodiments, the offset is between 12% and 16% of the total compartment width to optimize bulk flow. In some embodiments, the offset is between 10% and 18% of the total compartment width to optimize bulk flow. In some embodiments, the offset is between 8% and 20% of the total compartment width to optimize bulk flow. In some embodiments, the offset is between 6% and 22% of the total compartment width to optimize bulk flow. In some embodiments, the offset is between 4% and 24% of the total compartment width to optimize bulk flow. In some embodiments, the offset is between 2% and 26% of the total compartment width to optimize bulk flow.

In one aspect, a bioproduction mixing assembly is disclosed. The system may comprise a helical assembly including a first line and a second line, an impeller having a first end with first and second attachment positions and a second end with first and second attachment positions wherein the first attachment position of the first end is affixed to the first line and the first attachment position of the second end is affixed to the second line wherein the second attachment position of the first end is secured to the first line and the second attachment position of the second end is secured to the second line, the second attachment positions secured to slide along the lines while the mixing assembly is in operation. In some embodiments, the attachment positions are protrusions that engage a set of openings in the first and second lines and the openings for receiving the second attachment positions are oval shaped to allow movement of the protrusions along the length of the lines.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 34 illustrates a mixing system 3400 in accordance with one embodiment.

DETAILED DESCRIPTION

Description

Embodiments of systems, methods, and apparatuses for cell culture are described in the accompanying description and figures. In the figures, numerous specific details are set forth to provide a thorough understanding of certain embodiments. A skilled artisan will be able to appreciate that the fluid or cell culture media mixing system described herein may be used for a variety of applications including, but not limited to, buffer creation, media rehydration, cell culture, viral inactivation, and fermentation. Additionally, the skilled artisan will appreciate that certain embodiments may be practiced without these specific details. Furthermore, one skilled in the art will readily appreciate that the specific sequences in which methods are presented and performed are illustrative and it is contemplated that the sequences may be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in described various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequence may be varied and still remain within the spirit and scope of the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
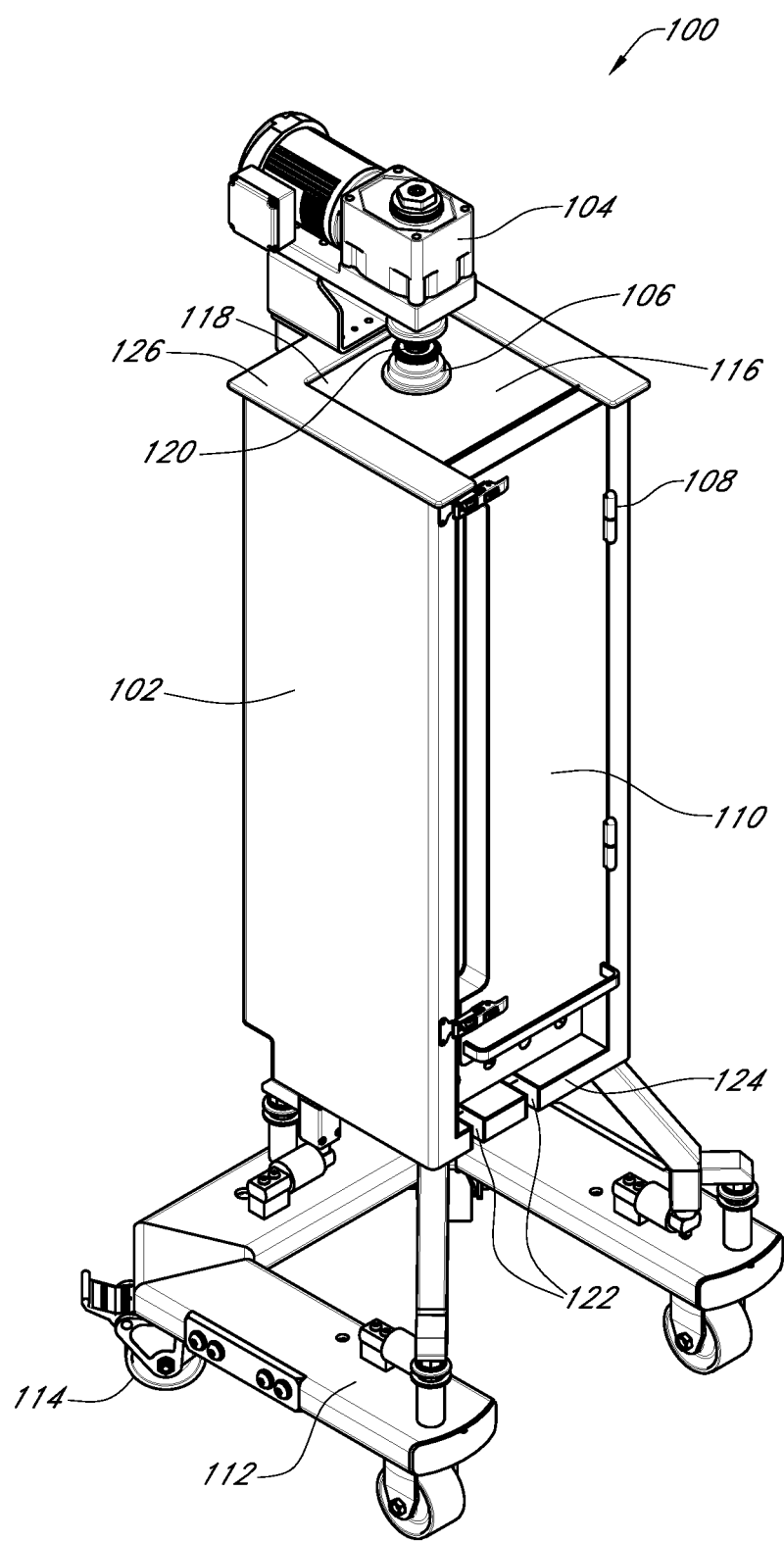
FIG. 1 illustrates a mixing system 100 in accordance with one embodiment.

FIG. 1 illustrates a fluid mixing system 100 according to various embodiments. The mixing system 100 generally comprises a rigid housing 102, a motor 104 mounted to the rigid housing 102, a first bearing assembly 106 in rotational communication with the motor 104 through a drive shaft 120 and providing rotational movement to the interior of a flexible compartment 118, a hinges 108 to secure a door 110 to the rigid housing 102 and provide enclosure for the flexible compartment 118, a rigid housing support 112 for the rigid housing 102 to mount thereto, and a support wheels 114 affixed to the rigid housing support 112 and provide mobility to the mixing. The rigid housing 102 may have rigid housing openings 122 cut into rigid housing floor 124 for retaining various ports 228 and a second bearing assembly 222 from the flexible compartment 218. In some embodiments, the rigid housing may be fixed in place and not require support wheels 114. In such embodiments, the rigid housing support 112 may be bolted to the bolt or simply held in place by the weight of the rigid housing 102.

Figure 2:
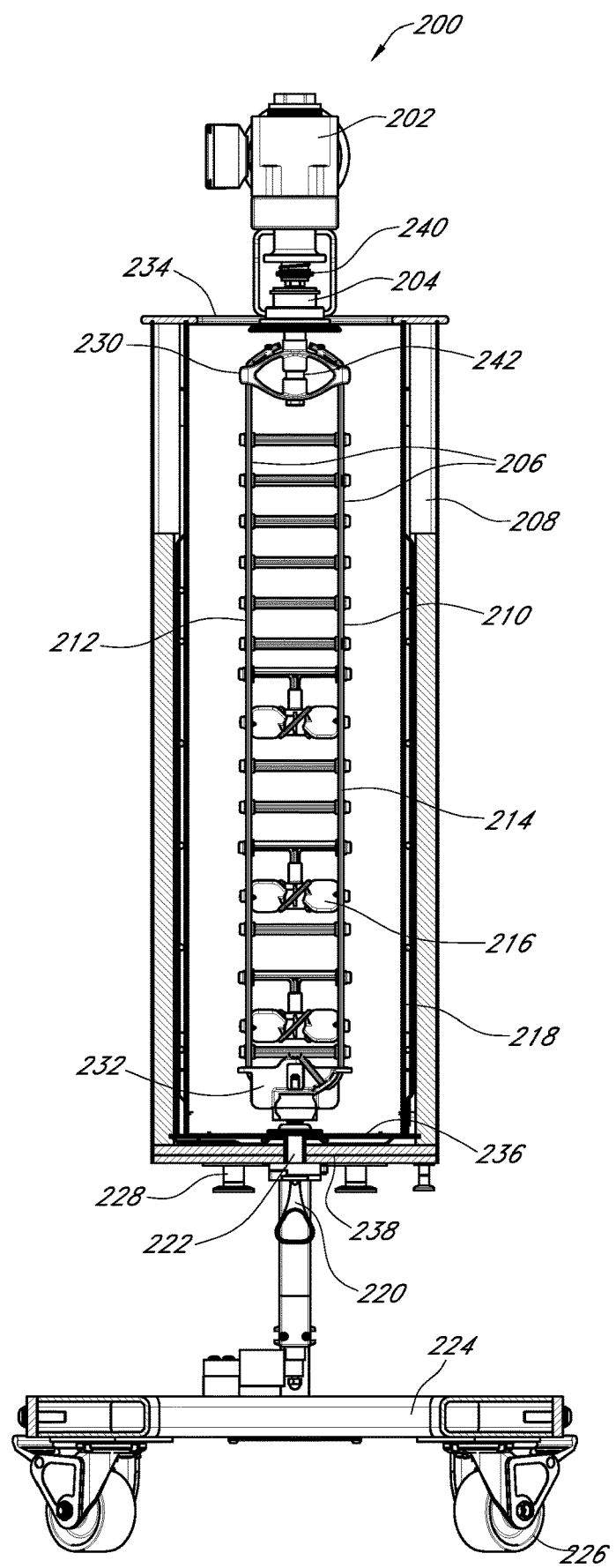
FIG. 2 illustrates a mixing system 200 in accordance with one embodiment.

FIG. 2 illustrates a cross sectional view of a fluid mixing system 200 according to various embodiments. The mixing system 200 comprises a motor 202 mounted to a rigid housing 208 having a drive shaft 120 that is in sterile, rotational communication to the interior of a flexible compartment 218 through a first bearing assembly 204. The mixing system 200 also comprises a helical assembly 214 comprised of a yoke 230 and a yoke/impeller 232 that act to suspend a driveline 206 between a first end 234 and second end 236 of the flexible compartment 218. The yoke/impeller 232 may be mounted to a second bearing assembly 222 to provide rotational movement to the helical assembly 214 on an opposing end of the flexible compartment 218. One or more impellers 216 may be mounted to the helical assembly 214 to provide mixing to a fluid within the flexible compartment 218. To facilitate installation of the flexible compartment 218 into the rigid housing 208 a pull handle 220 may be mounted to the second end 236 of the flexible compartment 218 and in some embodiments onto the second bearing assembly 222. The rigid housing 208 may be mounted to a rigid housing support 224 and support wheels 226 may be attached to the rigid housing support 224 to provide mobility to the mixing system 200. In various embodiments, the flexible compartment 218 further comprises at least one port 228 that may protrude through the rigid housing floor 124, 238.

In various embodiments, a user can open the door 110 to the rigid housing 102, 208 for easy installation of the flexible compartment 118, 218. As seen in FIG. 1, when the door 110 move to an open position the top surface 126 of the rigid housing 102, 208 may be completely open on the front face. The top surface 126 may make a "U" perimeter shape that comprises a back portion and two side portions that extend toward the door. While the door 110 is in the open configuration the flexible compartment 118, 218 may be moved into the chamber of the rigid housing 102, 208. The first bearing assembly 106, 204 located on the first end 116, 234 of the flexible compartment 118, 218 may then be inserted onto the drive shaft 120, 240. Additional disclosure relating to mounting the flexible compartment 118, 218 to the drive shaft 120 may be found in US 2017-0183617, filed on Dec. 28, 2016 which is incorporated herein by specific reference in its entirety. Hangers (not shown) attached to the rigid housing 102, 208 may be hooked onto loops (not shown) on the flexible compartment 118, 218 to further secure the flexible compartment 118, 218 to the top surface 126 of the rigid housing 102, 208. Once the first end 116 of the flexible compartment 118, 218 is secured to the top surface 126 of the rigid housing 102, 208 the second end 236 may slide into the rigid housing floor 124, 238. In various embodiments, the flexible compartment 118, 218 will comprise one or more ports 228 and a second bearing assembly 222 that protrude from the exterior of the second end 236 of the flexible compartment 118, 218. Rigid housing opening 122 in the rigid housing floor 124, 238 may be configured to accept the ports 228 and second bearing assembly 222, thereby, securing the second end 236 of the flexible compartment 118, 218 to the rigid housing floor 124, 238 of the rigid housing 102, 208. In some embodiments, a closure (not shown) can cover the rigid housing opening 122 to further secure the ports 228 and second bearing assembly 222 to the rigid housing floor 124, 238 of the rigid housing 102, 208. In various embodiments, a user can grip the pull handle 220 located at the second end 236 of the flexible compartment 118, 218 to pull the flexible compartment 118, 218 into place within the rigid housing 102, 208.

In various embodiments, once installation has been accomplished a fluid may be fed into the sterile flexible compartment 118, 218 which may require mixing. The motor 104, 202 may be activated using a controller (not shown) which may then rotate the drive shaft 120, 240 which was inserted previously into the first bearing assembly 106. In some embodiments, there may be a single drive shaft 120, 240 that protrudes from the motor 104, 202 and into the sterile flexible compartment 118, 218 and in other embodiments the first bearing assembly 106 will be closed off and have a second drive shaft portion 242 that extends from the first bearing assembly 106. In various embodiments, the drive shaft 120 or second drive shaft portion 242 will mount to a yoke 230 that works to space apart a first line 210 and a second line 212 of a driveline 206. On the second end 236 of the flexible compartment 118, 218 there may be a second bearing assembly 222 comprising a yoke/impeller 232 that operates to suspend the other ends of the first line 210 and the second line 212 as well as provide mixing as it rotates. The second bearing assembly 222 may be designed to provide rotational movement so that rotational to allow the helical assembly 214 to freely rotate as the motor 104, 202 drives the helical assembly 214 from the opposing end. One or more impellers 216 may provide mixing in addition to the yoke/impeller 232.

In various embodiments, an added advantage of the yoke/impeller 232 is to provide very low volume mixing. For example, a bioreaction may require a small volume at the beginning of a reaction and the fluid volume may be increased as the bioreaction matures. Currently available bioreactors have limitations with scale-up which the present embodiment reduces. Impellers 216 may be affixed at various locations on the helical assembly 214 when considering optimal scale up for a given bioreactor as well. In some embodiments, the yoke/impeller 232 may maintain a homogenous mix in the fluid at very low volume during a draining process.

Figure 3:
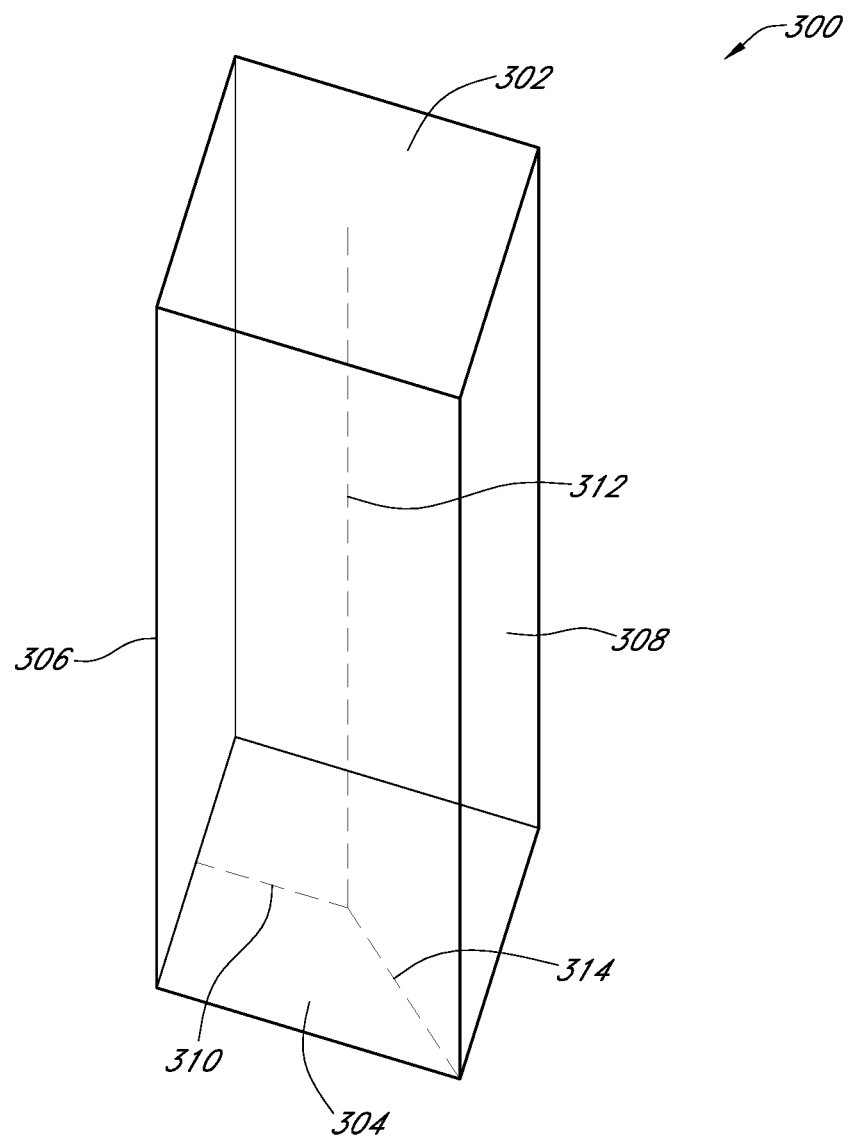
FIG. 3 illustrates a flexible compartment 300 in accordance with one embodiment.

FIG. 3 illustrates a flexible compartment 300 according to various embodiments. The flexible compartment 300 comprises a first end 302, an opposing second end 304, a sidewall 306 connecting the first end 302 and the second end 304, at least three panels 308 joining the first end 302 and the second end 304, a sidewall line 310, a centerline 312, and a cornerline 314.

In various embodiments, the centerline 312 is an indicator of a vertical axis running from the center of the first end 302 to the center of the second end 304 of the flexible compartment 300. For example, the centerline 312 may be placed such that the length from the centerline 312 to opposing panels 308 is equal. In various embodiments, a sidewall line 310 may be an indicator of a plane running from the first end 234 to the second end 304 of the flexible compartment 300 and extend from the centerline 312 to the mid-point of a panel 308. In various embodiments, a cornerline 314 may be an indicator of a plane running form the first end 302 to the second end 236 of the flexible compartment 300 and extend from the centerline 312 to where two panels 308 are joined to form a corner. In various embodiments, the indicators listed above may be used to determine where the helical assembly 214 will reside within the flexible compartment 300 when reducing dead zones and increasing bulk fluid and, thereby, increasing overall mixing efficiency within the mixing system 100, 200.

Figure 4:
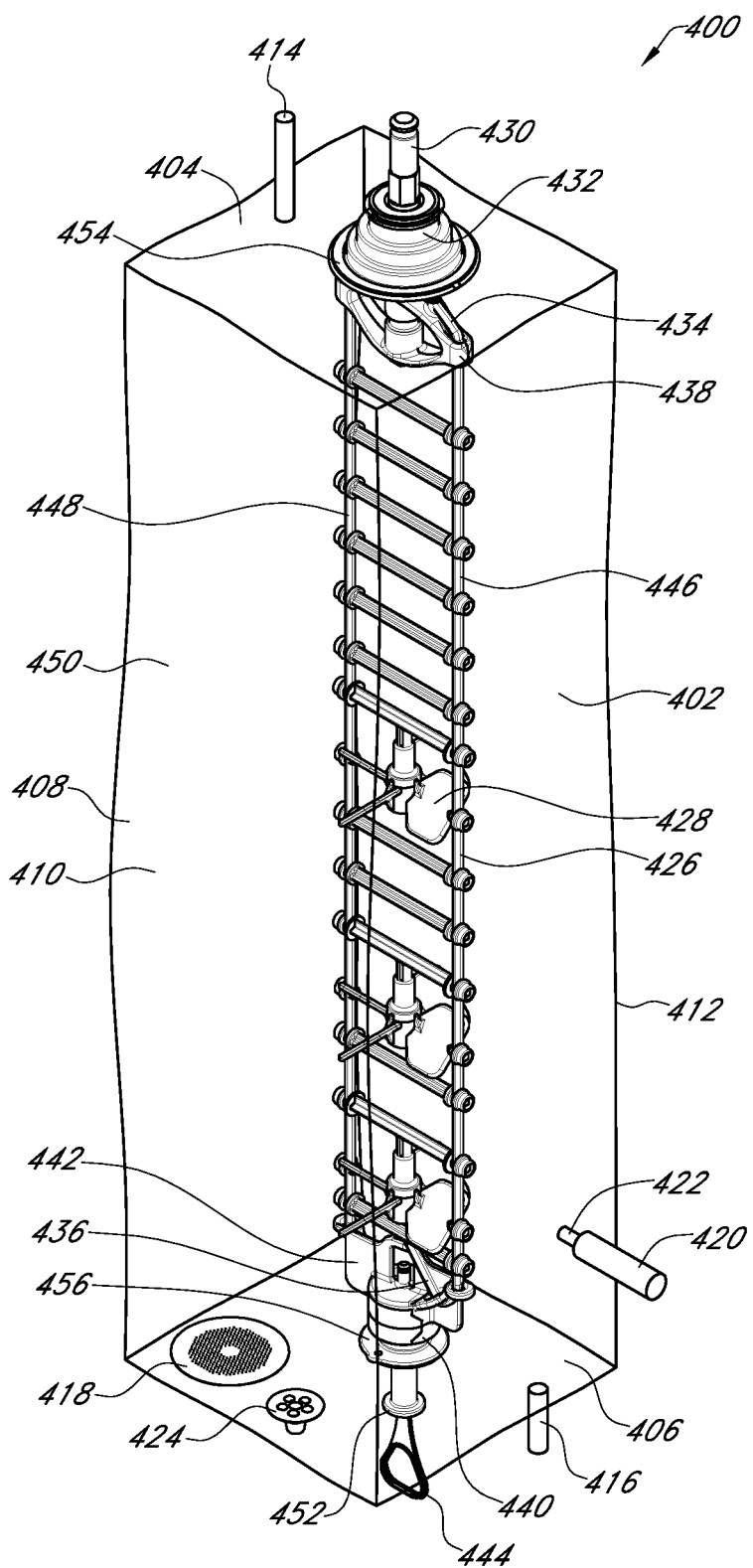
FIG. 4 illustrates a mixing system 400 having a helical assembly 426 situated along a centerline in accordance with one embodiment.
Figure 5:
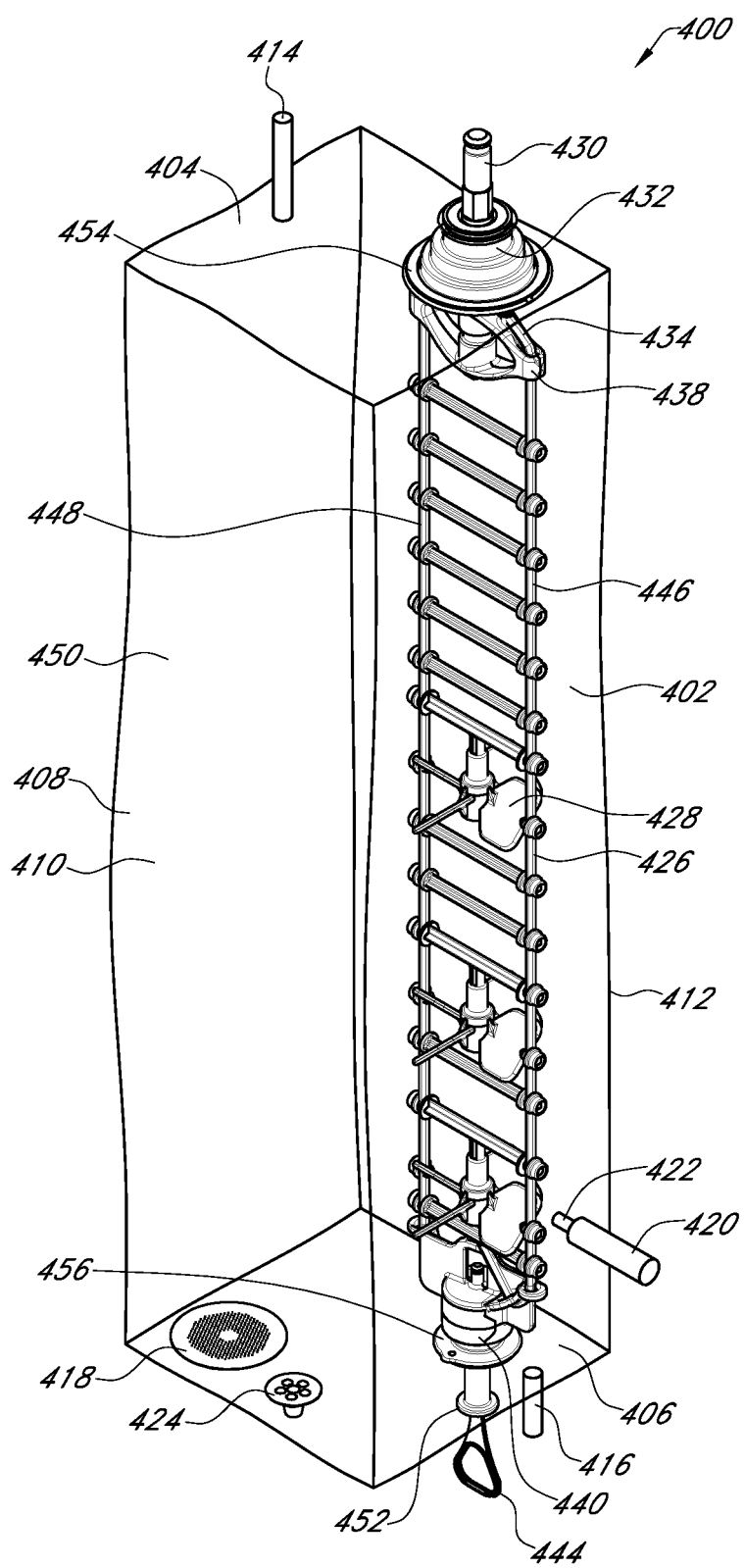
FIG. 5 illustrates a mixing system 400 having a helical assembly 426 situated along a cornerline in accordance with one embodiment.
Figure 6:
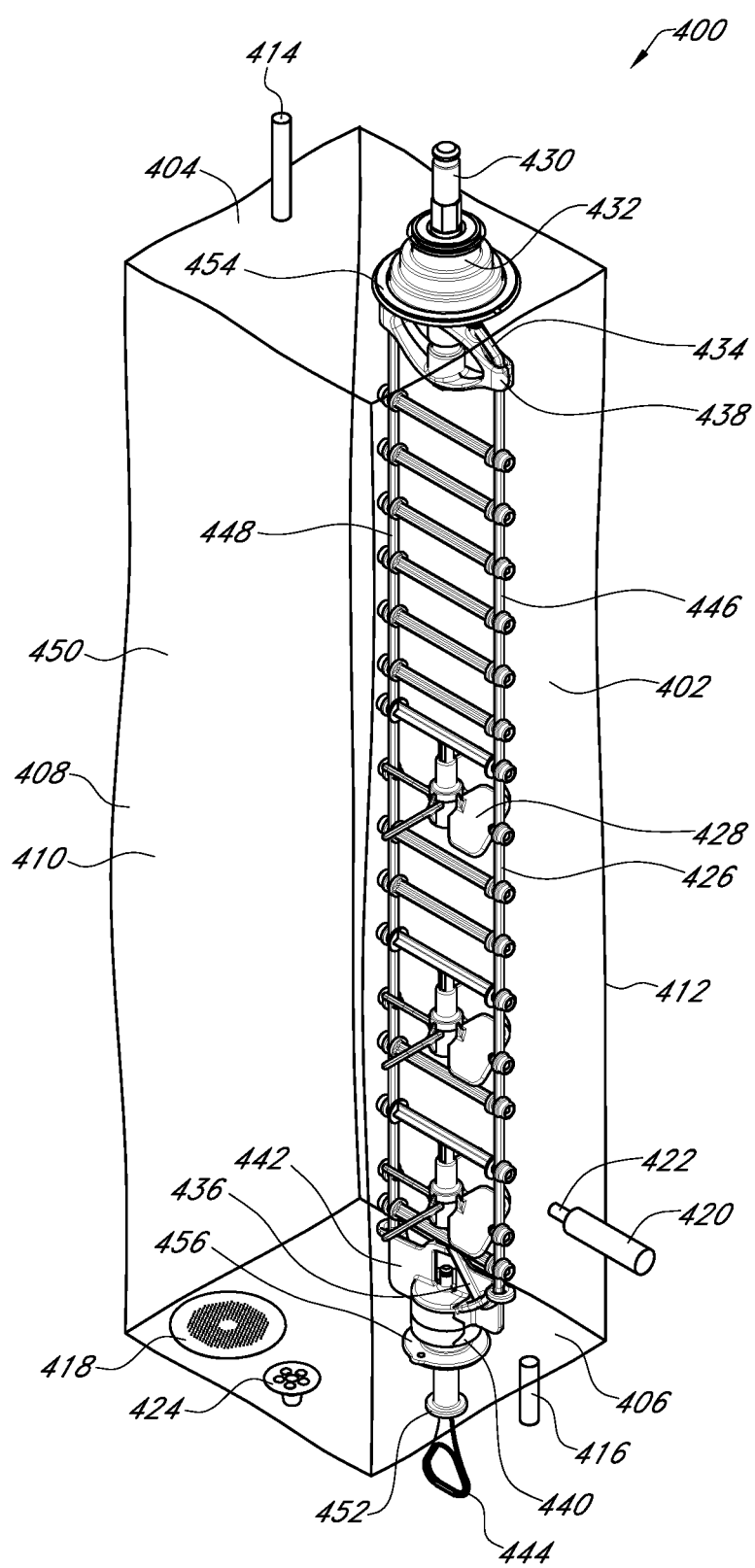
FIG. 6 illustrates a mixing system 400 having a helical assembly 426 situated along a sidewall line in accordance with one embodiment.

FIGS. 4, 5, and 6 illustrate mixing systems 400, 500 according to various embodiments. The mixing systems 400, 500 comprise a flexible compartment 402 having a first end 404 and an opposing second end 406 that are joined together by a sidewall 408 having at least three panels 410 and sidewall corners 412 where the panels meet. The flexible compartment 402 may further include one or more inlets 414, one or more outlets 416, one or more spargers 418, one or more sensor ports 420 that optionally contain a sensor 422, and a drain 424. In various embodiments a helical assembly 426 may be suspended between the first end 434 and the second end 436 of the flexible compartment 402 and have one or more impellers 428 positioned thereto. In various embodiments, a drive shaft 430 may project into a first bearing assembly 432 and the first bearing assembly 106 may provide a sterile connection between the drive shaft 430 on the exterior of the flexible compartment 402 to a yoke on the interior of the flexible compartment 402. In various embodiments, a second bearing assembly 440 may be positioned on the second end 406 of the flexible compartment 402 and may include a pull handle 444 projecting onto the exterior portion of the flexible compartment 402 and on the opposing/interior portion the second bearing assembly 440 may connect to a yoke/impeller 442. In various embodiments, the helical assembly 426 may be comprised of a first line 446 and a second line 448 that each have a first end 434 connected to a yoke 438 and a second end 436 connected to a yoke/impeller 442 and during operation the rotational movement may be applied to mix a fluid 450 within the flexible compartment 402. In various embodiments, the flexible compartment 402 may include an attachment ring 452 either affixed to or molded as part of the second bearing assembly 222 used can slide into a retention device on the rigid housing 102, 208 during installation. In some embodiments, the design may include a snap ring that fits onto a pin and may slide into the bottom port of the flexible compartment 402.

In various embodiments, the flexible compartment 402 may include one or more inlets 414 and outlets 416. Inlets 414 may be used during the installation process to add a gas to the flexible compartment 402 in order to inflate the flexible compartment 402 to its working volume. Additionally, inlets 414 may be used to introduce dry media, buffers, liquid nutrients, or anything else requiring mixing. Outlet 416 may be used to harvest the contents of the flexible compartment 402 after a mixing process is complete or a bioreaction has achieved a desired state. Additionally, a drain 424 may be used to empty the waste within the flexible compartment 402. There are various ways known in the art for attaching inlets 414, outlets 416, and drains 424. A common technique is weld the component to the flexible compartment 402. For example the component may include a polymer that can be welded to the polymer comprising the flexible compartment 402. US 2017-0183617 includes a list of common weldable materials used to produce flexible compartments 402. For example, flexible compartment 402 can be formed from one or more sheets of a polymeric film.

In various embodiments, sensors 422 may be used to monitor the environmental conditions within the flexible compartment 402. There are a variety of sensors and sensor ports 420 available on the market including those described in US 2008-0032389 filed on Mar. 26, 2007 which is incorporated herein by specific reference in its entirety. Various techniques are described in the above cited reference disclosing ways to bond sensor ports 420 to flexible compartments 402 using welding and adhesion methods.

In various embodiments, the mixing system 400, 500, 600 described herein may be used for cultivating cells and then harvesting the cells in their entirety or harvesting a cell byproduct such as a protein or enzyme. Such bioreactions often require introduction of a gas which is typically done with using a sparger 418 in the field of bioproduction. A variety of sparger 418 designs and their methods of attachment are described in US 2013-0082410 filed on Sep. 28, 2012 which is incorporated herein by specific reference in its entirety.

In various embodiments, the first bearing assembly 432 and the second bearing assembly 440 may include a first annular sealing flange 454 and a second annular sealing flange 456 that may be sealed to openings on the flexible compartment 402 by welding or adhesive around the perimeter. As disclosed in US 2017-0183617 this allows for rotational movement of a hub while an outer casing remains fixed to the flexible compartment 402 allowing the helical assembly 426 to freely rotate within the flexible compartment 402 while remaining sterile to the exterior.

In various embodiments, an attachment ring 452 may be engageable to a retention device on the rigid housing 102, 208. The retention device may take the form of a bracket or some other physical structure capable of retaining and/or restricting the movement of the attachment ring 452. Generally, during the installation process a user will pull the pull handle 444 into the rigid housing opening 122 in order to facilitate the attachment ring 452 and retention device interaction in order to complete flexible compartment 402 installation.

In various embodiments, the optimal location of the helical assembly 426 relative to the flexible compartment 402 will be along the centerline 312 as depicted in FIG. 4.

In various embodiments, the optimal location of the helical assembly 426 relative to the flexible compartment 402 will be along the cornerline 314 as depicted in FIG. 5.

In various embodiments, the optimal location of the helical assembly 426 relative to the flexible compartment 402 will be along the sidewall line 310 as depicted in FIG. 6.

Figure 7:
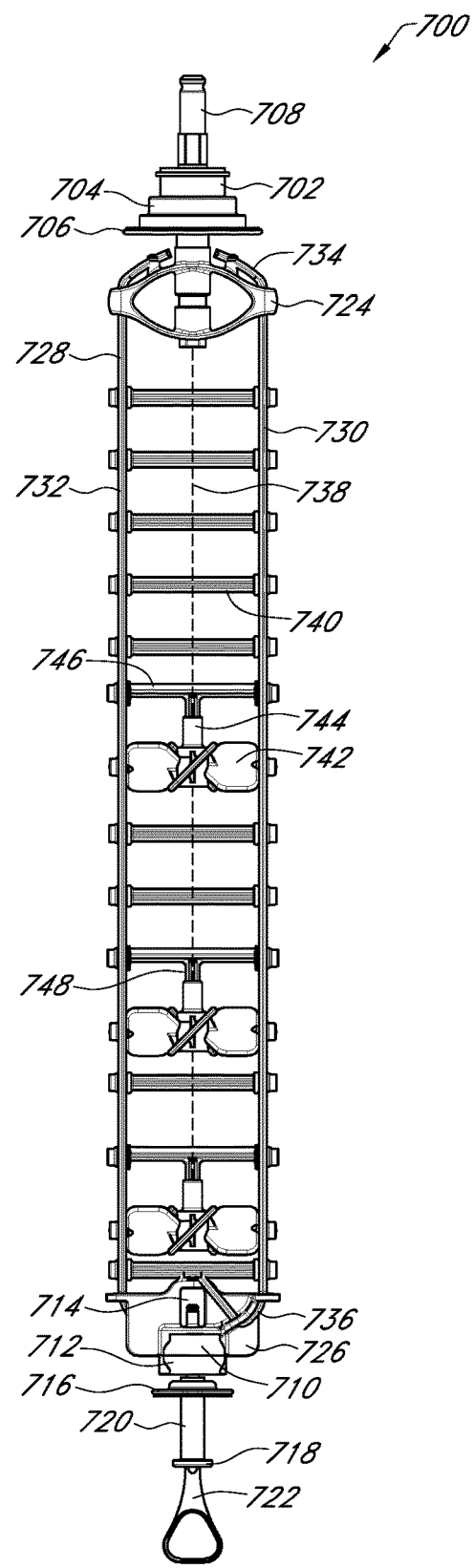
FIG. 7 illustrates a helical assembly 700 in accordance with one embodiment.

FIG. 7 illustrates a helical assembly 700 according to various embodiments. The helical assembly 700 comprises a first bearing assembly 702 that may include an outer casing 704, a first annular sealing flange 706, a drive shaft 708, a second bearing assembly 710 that may include a second annular sealing flange 716, an attachment ring 718, a retaining post 720, the helical assembly 700 further including a yoke 724, a yoke/impeller 726, a driveline 728, a first line 730, a second line 732, a first end 734, a second end 736, a driveline axis 738, a rung 740, an impeller 742, a receiver 744, a stabilizer 746, and a stem 748.

In various embodiments, the first bearing assembly 702 may include an outer casing 704 that is configured to remain in a fixed configuration. The outer casing 704 may include a first annular sealing flange 706 having a perimeter designed to be welded or adhered onto an opposing perimeter of an opening in a flexible compartment 402. The outer casing 704 may be designed to house a drive shaft 708 that may rotate freely relative to the outer casing 704.

In various embodiments, the second bearing assembly 710 may include an outer casing 712 that is configured to remain in a fixed configuration. The outer casing 712 may include a first second annular sealing flange 716 having a perimeter designed to be welded or adhered onto an opposing perimeter of an opening in a flexible compartment 402. The outer casing 712 may be designed to house a drive shaft 714 that may rotate freely relative to the outer casing 712. Additionally, the second bearing assembly 710 may include a retaining post 720 extending away from the second annular sealing flange 716. The retaining post 720 may have a first end affixed to the second annular sealing flange 716 and a second end affixed to an attachment ring 718 where the retaining post 720 is may be slightly longer than the thickness of the rigid housing floor 238 in order to fit within the rigid housing opening 122. In various embodiments, the second annular sealing flange 716 and the attachment ring 718 may include diameters that are slightly larger than the rigid housing opening 122 to restrict vertical movement of the flexible compartment 402. In various embodiments, a user can position the retaining post 720 within the rigid housing opening 122 and use the pull handle 722 to secure the flexible compartment 402 within the rigid housing 102, 208.

In various embodiments, a yoke 724 may be positioned in the interior of the flexible compartment 402 adjacent to the first end 404 and in physical communication with the first bearing assembly 702 and the yoke/impeller 726 may be positioned in the interior of the flexible compartment 402 adjacent to the second end 736 and in physical communication with the second bearing assembly 710. In various embodiments the driveline 728 may be suspended between the yoke 724 and the yoke/impeller 726 to provide a rotational structure for securing impellers 742 thereto. In various embodiments, the driveline 728 may include a first line 730 and a second line 732 which may be joined by a plurality of rungs 740. The yoke 724, yoke/impeller 726, and plurality of rungs 740 may provide lateral spacing about a driveline axis 738.

In various embodiments, rungs 740 may be attached or detached as required by the specific application. In operation the rungs 740 provide mixing of a fluid 450, therefore, mixing characteristics in a given mixing system 100, 200, 300, 400, 500, 600 may be altered depending on the number of rungs 740 used.

In various embodiments, stabilizers 746 and impellers 742 can replace rungs 740 to not only provide stability and spacing about the driveline axis 738, but also provide additional mixing within the flexible compartment 402. In some embodiments, an impeller 742 can attach to the first line 730 and the second line 732 and a stabilizer 746 may be positioned one rung position away and also be attached to the first line 730 and the second line 732. When the an impeller 742 and stabilizer 746 are positioned adjacent to one another they can interact through a tubular shaped receiver on the impeller 742 and a stem 748 projecting into the receiver 744 from the mid-point of the stabilizer 746. In various embodiments, the interaction between the stabilizer 746 and impeller 742 act to keep the impeller 742 blades optimally aligned while the mixing system 100 system is in operation. In some embodiments, it may be useful to allow the impeller 742 to align itself (without the stabilizer 746) according to the forces acting upon it as the helical assembly 700 rotates, however, in many applications the resulting impeller 742 orientation would be undesirable because bulk fluid flow would be reduced.

Figure 8:
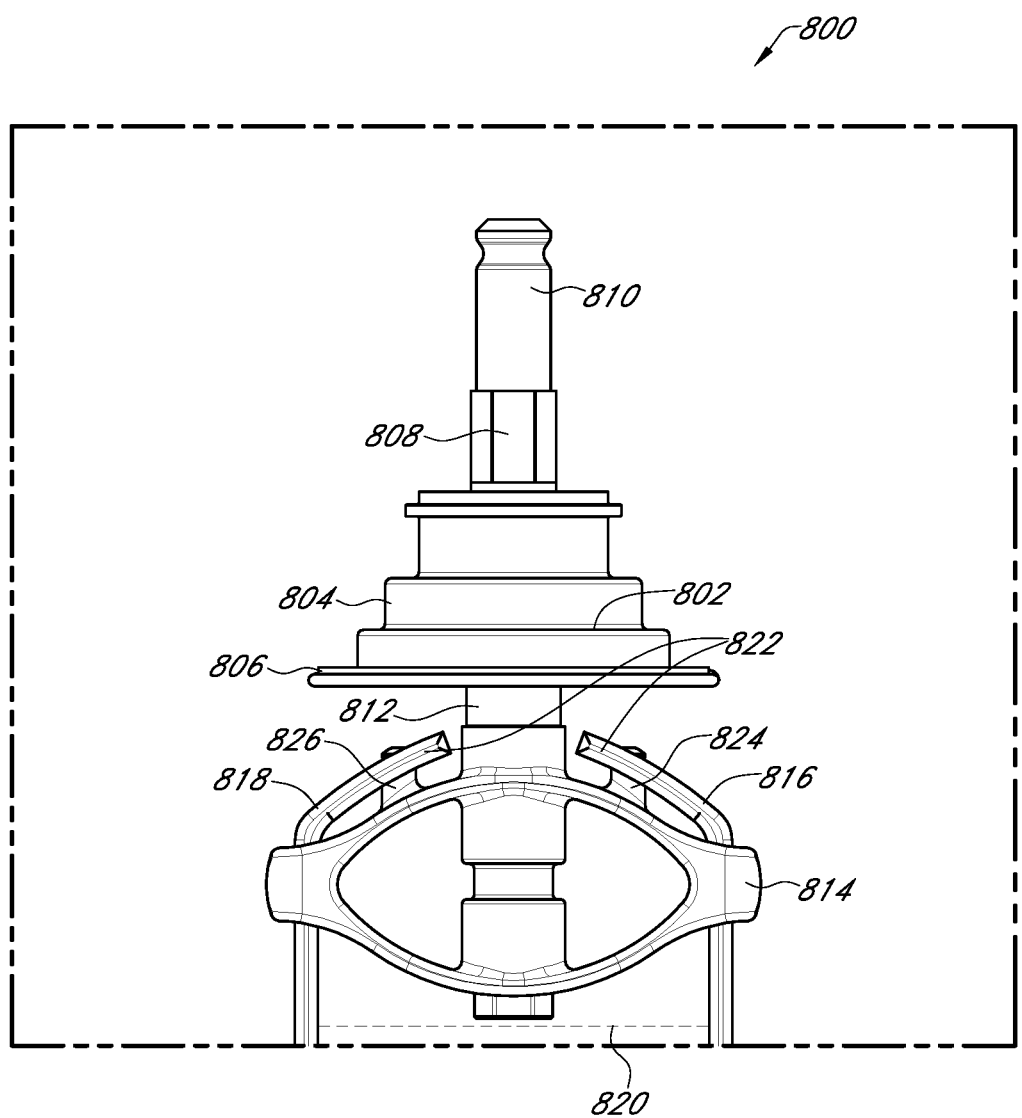
FIG. 8 illustrates an enlarged view of first bearing assembly 802 and a portion of a helical assembly 800 in accordance with one embodiment.

FIG. 8 illustrates a helical assembly 800 according to various embodiments. The helical assembly 800 may comprise a first bearing assembly 802 having an outer casing 804, a first annular sealing flange 806, a polygonal insertion portion 808, a first driveshaft end 810, a second driveshaft end 812, a yoke 814 retaining a first line 816 and a second line 818 at a helical width 820 with the a first ends 822 of the lines affixed to, a first peg 824, and a second peg 826.

In various embodiments, the yoke 814 may have two openings to thread first and second lines 816, 818 through. The first line 816 and the second line 818 each have a plurality of openings for inserting rungs 740, stabilizers 746, and impellers 742 as well as openings at or near the first ends 822 of the lines 816, 818. The purpose of those openings may be to affix the lines 816, 818 onto first and second pegs 824, 826. In some embodiments, simply inserting the pegs 824, 826 through the openings is enough to secure the lines 816, 818 to the yoke 814, but in some circumstances adhesive, welding, or caps may be incorporated to ensure a secure connection. Such caps may resemble rung caps.

In various embodiments, the polygonal insertion portion 808 services to interact with an opposing female connection (not shown) that may be in physical communication with the motor 104, 202. A variety of connections and bearing assemblies are disclosed in US 2011-0188922 filed on Feb. 1, 2010 which is incorporated herein by specific reference in its entirety. In some embodiments, there may be a male end on the bearing hub and a female end on the yoke.

Figure 9:
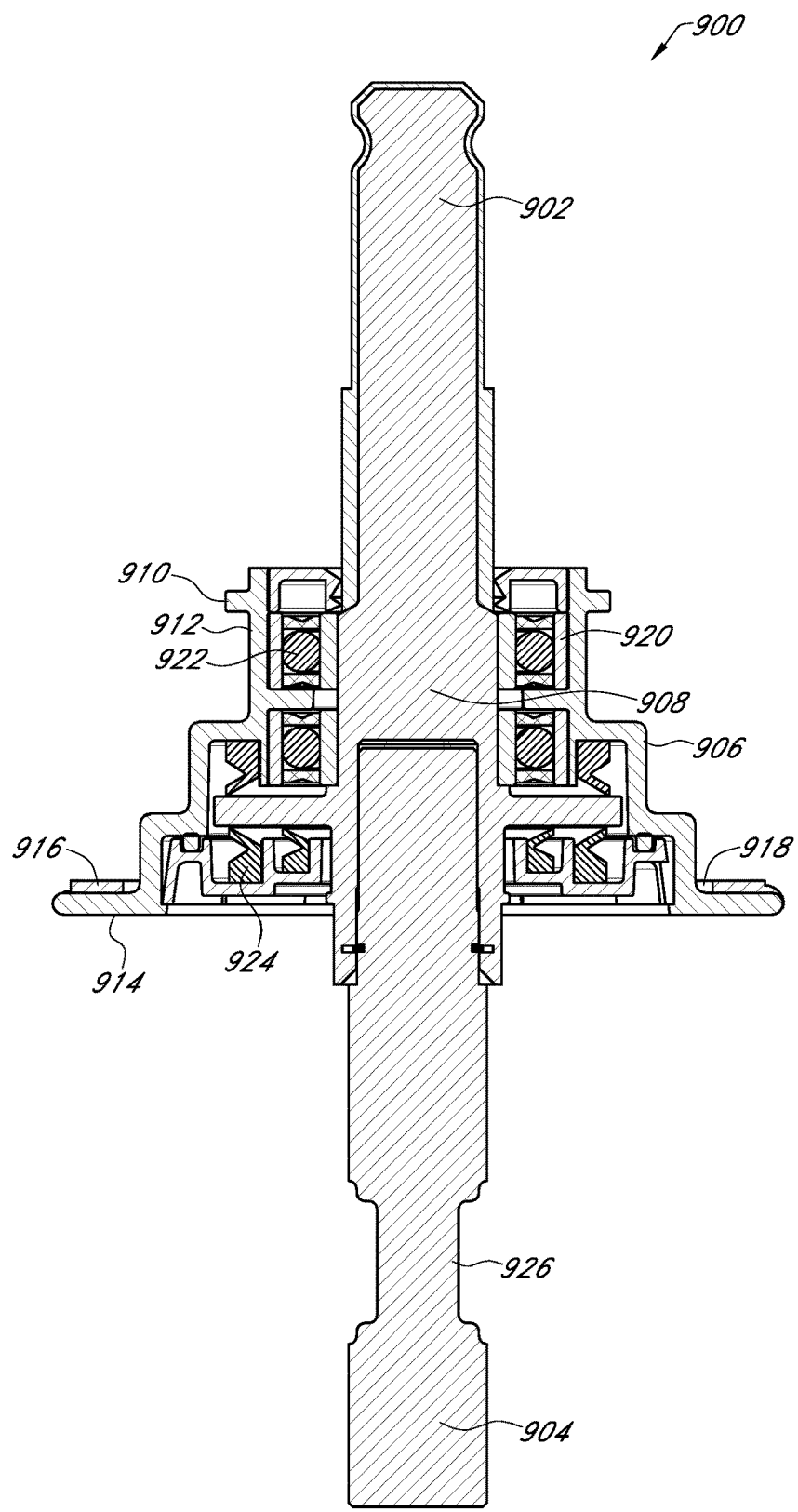
FIG. 9 illustrates a cross sectional view of a first bearing assembly 900 in accordance with one embodiment.

FIG. 9 illustrates a first bearing assembly 900 according to various embodiments. The first bearing assembly 900 may comprise a first drive shaft end 902, a second driveshaft end 904, an outer casing 906, a hub 908, an annular mounting flange 910, a mounting recess 912, a first annular sealing flange 914 in physical communication with a flexible container 916, an opening 918, a bearing unit 920, a ball bearing 922, and a seal 924.

In various embodiments, an outer casing 906 may house a hub 908 that connects to a first drive shaft end 902 and a second driveshaft end 904. In some embodiments the first drive shaft end 902, hub 908, and second driveshaft end 904 may be molded from a single piece of material (polymer, metal, etc.). In some embodiments, they may be separate pieces that may be adhered or welded together. In various embodiments, the first drive shaft end 902 protrudes outside of the flexible container 916 and the second driveshaft end 904 protrudes into the flexible container 916 through a sterile, rotationally mobile assembly.

In various embodiments, the first bearing assembly 900 may include an outer casing 906 that includes an annular mounting flange 910 and a mounting recess 912. A member located on the motor 104, 202 assembly (not shown) may serve to insert into the mounting recess 912, thereby, restricting movement of the first bearing assembly 900 allowing the motor 104, 202 to transfer rotational movement to the first drive shaft end 902, whereby, the attached hub 908 may transfer the rotational movement to the second first drive shaft end 902 within the flexible container 916 causing the helical assembly 214, 426, 700, 800 to mix a fluid 450 within the flexible container 916.

In various embodiments, rotational movement is facilitated by one or more bearing units 920 located between the outer casing 906 and the hub 908. In most embodiments, the bearing unit 920 may include one or more ball bearings 922.

In various embodiments, the sterile seal is created using one or more seals 924 located between the outer casing 906 and hub 908.

In various embodiments, the first bearing assembly 900 may be inserted into an opening 918 in the flexible container 916. During the manufacturing process of the flexible container 916 helical assembly 800 a first annular sealing flange 914 may abut the perimeter of the flexible container 916 encircling the first bearing assembly 900. The first annular sealing flange 914 and perimeter of the opening 918 may then be welded or adhered together to create a sterile seal.

In various embodiments, the second first drive shaft end 902 may include a yoke recess 926 which serves as a mounting point for the yoke 814. The yoke 814 may include a corresponding protrusion and affix to the yoke recess through frictional interaction. In some embodiments, the yoke 814 may be adhered or welded to the yoke recess 926. In some embodiments, the yoke 814 may be attached to the bearing assembly using a snap ring. Such an embodiments, may include a pin assembly.

Figure 10:
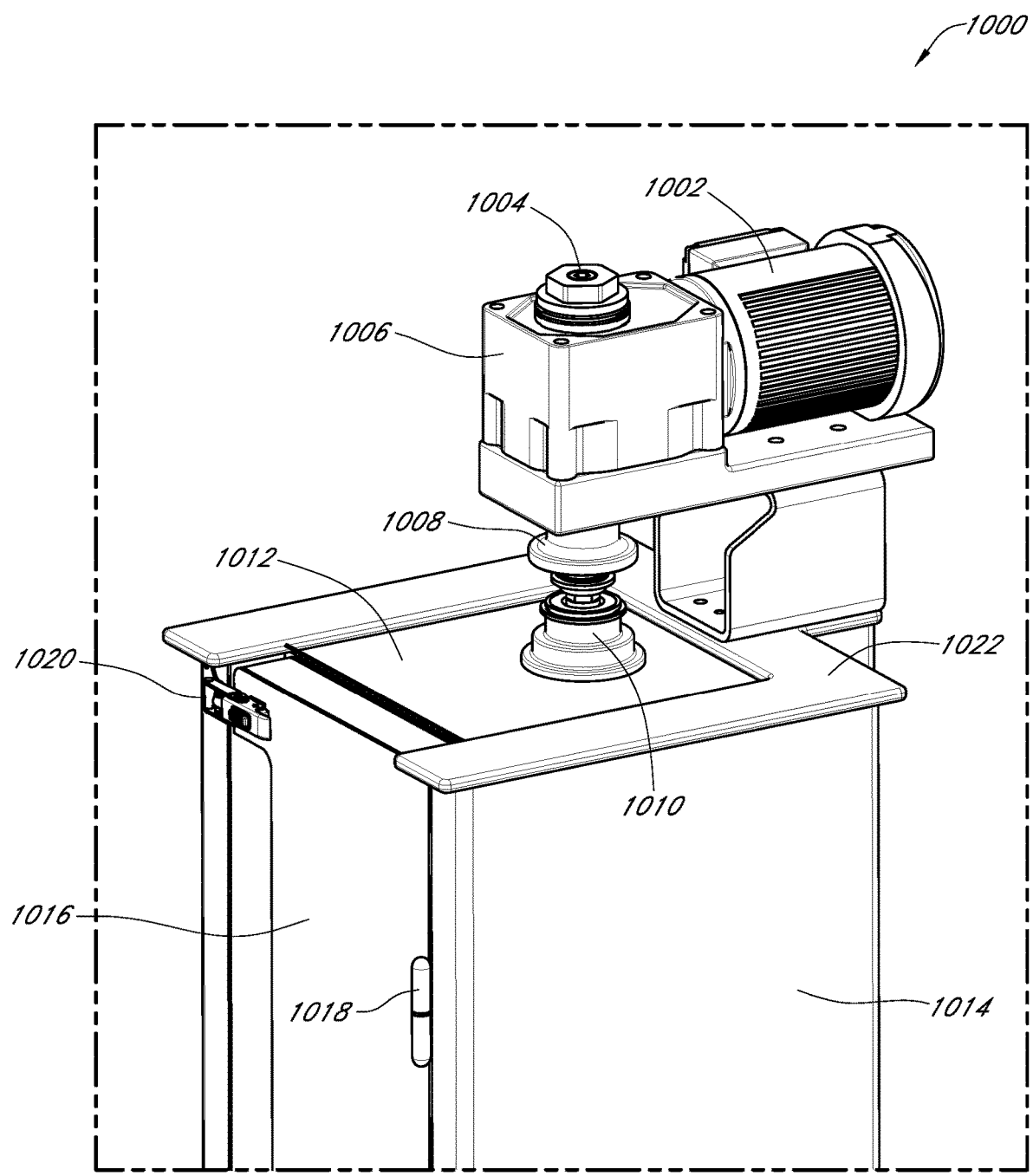
FIG. 10 illustrates a mixing system 1000 in accordance with one embodiment.
Figure 11:
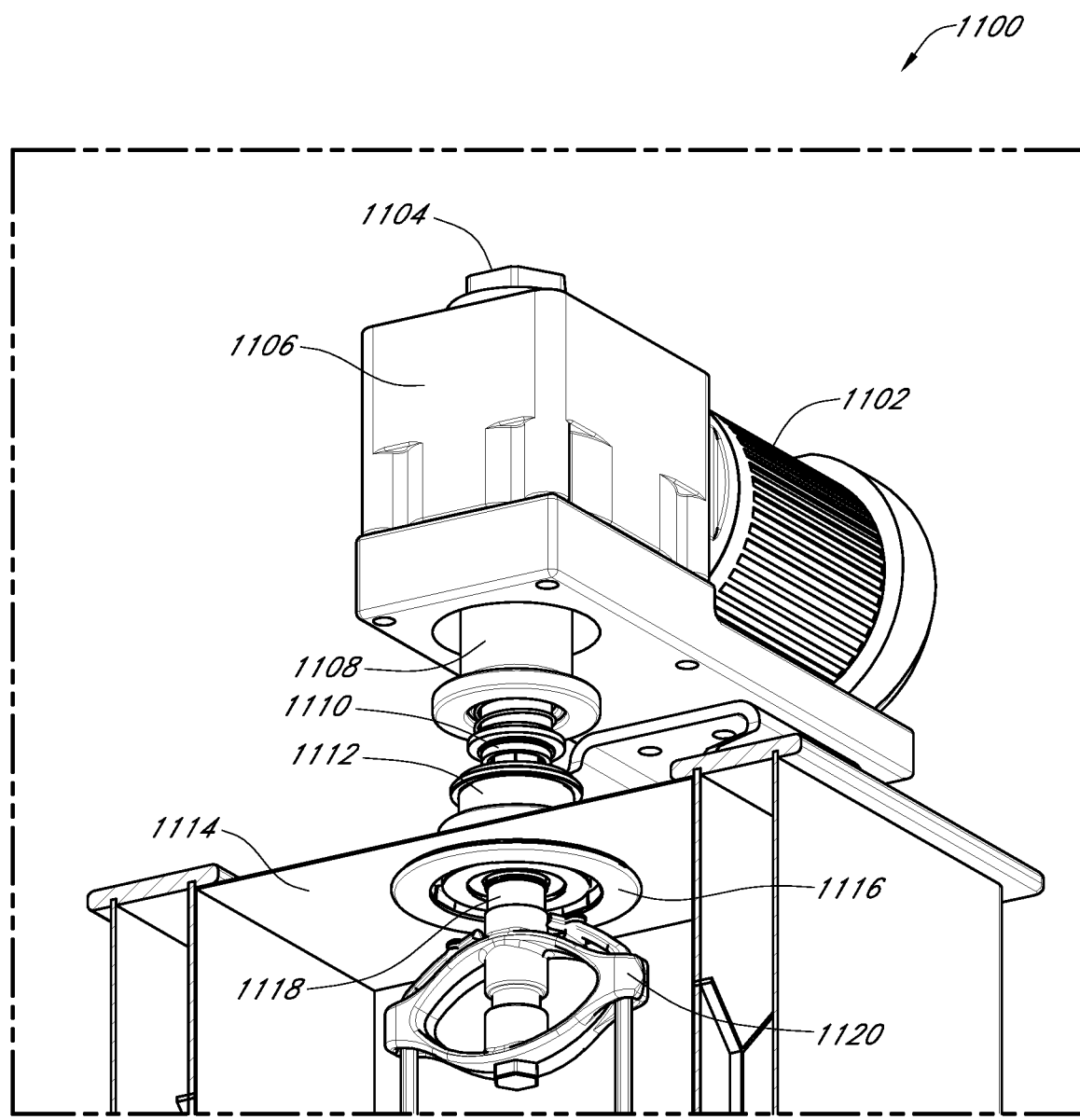
FIG. 11 illustrates a mixing system 1100 in accordance with one embodiment.

FIGS. 10 and 11 illustrate a mixing system 1000, 1100 according to various embodiments. The mixing system 1000 may comprise a motor 1002, 1102 connected to a gearbox assembly 1006, 1106. A drive shaft motor end 1004 may protrude from the gearbox assembly 1006, 1106 and be capped with a nut 1104. The gearbox assembly 1006, 1106 may deliver rotational energy to a first bearing assembly mount 1008, 1108 that is designed to accept an inserted first driveshaft first drive shaft end 1110. In various embodiments, the rotational power is transferred from the gearbox assembly 1006, 1106 the first bearing assembly mount 1008, 1108 and into the flexible compartment 1012, 1114 through a first bearing assembly 1010, 1112 that is welded onto the flexible compartment 1012, 1114 at a first annular mounting flange 1116. The second drive shaft end 1118 is in rotational communication with the first bearing assembly, 1010, 1112 and causes the yoke 1120 to rotate.

In various embodiments, the flexible compartment 1012, 1114 may be installed into a rigid housing 1014 that may provide support to the flexible compartment 1012, 1114 when a fluid is present. The flexible compartment 1012, 1114 may be secured inside of the rigid housing 1014 by inserted the flexible compartment 1012, 1114 into a cavity of the rigid housing 1014 and then by closing a door 1016 after insertion by swinging the door 1016 on hinges and later secured the door 1016 in the closed position by changing a latch 1020 from an open configuration to a closed configuration. In various embodiments, an end of the rigid housing 1014 may be substantially open and merely have a rigid housing rail 1022 acting as a ceiling.

Figure 12:
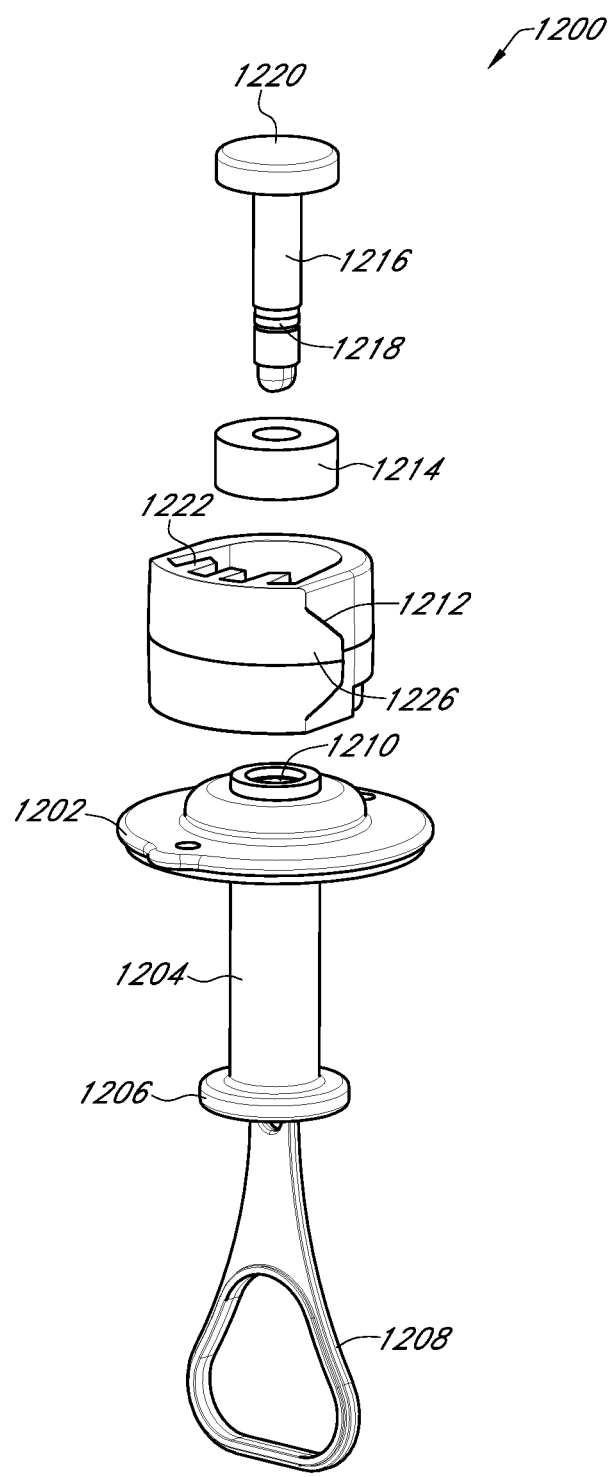
FIG. 12 illustrates a second bearing assembly 1200 in accordance with one embodiment.

FIG. 12 illustrates a second bearing assembly 1200 according to various embodiments. The second bearing assembly 1200 may comprise a second annular sealing flange 1202 which includes a retaining post 1204, an attachment ring 1206, a pull handle 1208, and a thrust pin receiver 1210. The second bearing assembly 1200 further includes a bearing cup 1212, a thrust bearing 1214, a thrust pin 1216, a snap recess 1218, and a pin head 1220.

In various embodiments, the second bearing assembly does not require transfer of rotational movement from the exterior of the flexible container 916 to the interior of the flexible container 916. However, in some embodiments, the second bearing assembly 1200 may resemble the first bearing assembly 900 such that it may be driven by a motor 104, 202 on the exterior of the flexible container 916.

In the various embodiments that do not require exterior transfer of rotational movement, the second bearing assembly 1200 may include a thrust pin 1216 retained by a thrust pin receiver 1210 by a snap recess 1218. In some embodiments, the thrust pin 1216 may insert through a thrust bearing 1214 and the thrust bearing 1214 may be positioned on the interior of a bearing cup 1212, thereby, allowing free rotational movement of the bearing cup 1212. In some embodiments, the bearing cup 1212 affixes to the yoke/impeller 726 and as the motor 104, motor 202 drives the hub 908 and transfers rotational power through the helical assembly 800 the bearing cup 1212 also rotates allowing for efficient mixing of a fluid 450. In various embodiments the thrust pin 1216 includes a pin head 1220 that may serve to prevent the thrust bearing 1214 and bearing cup 1212 from detaching from the thrust pin 1216.

In various embodiments, the bearing cup 1212 affixes to the yoke/impeller 726, thereby allowing free rotation of the yoke/impeller 726. In some embodiments, the bearing cup 1212 may be adhered or welded to the yoke/impeller 726. In other embodiments, the bearing cup 1212 may include teeth 1222, protrusions, or hooks 1026 that physically couple the bearing cup 1212 to the yoke/impeller 726.

Figure 13:
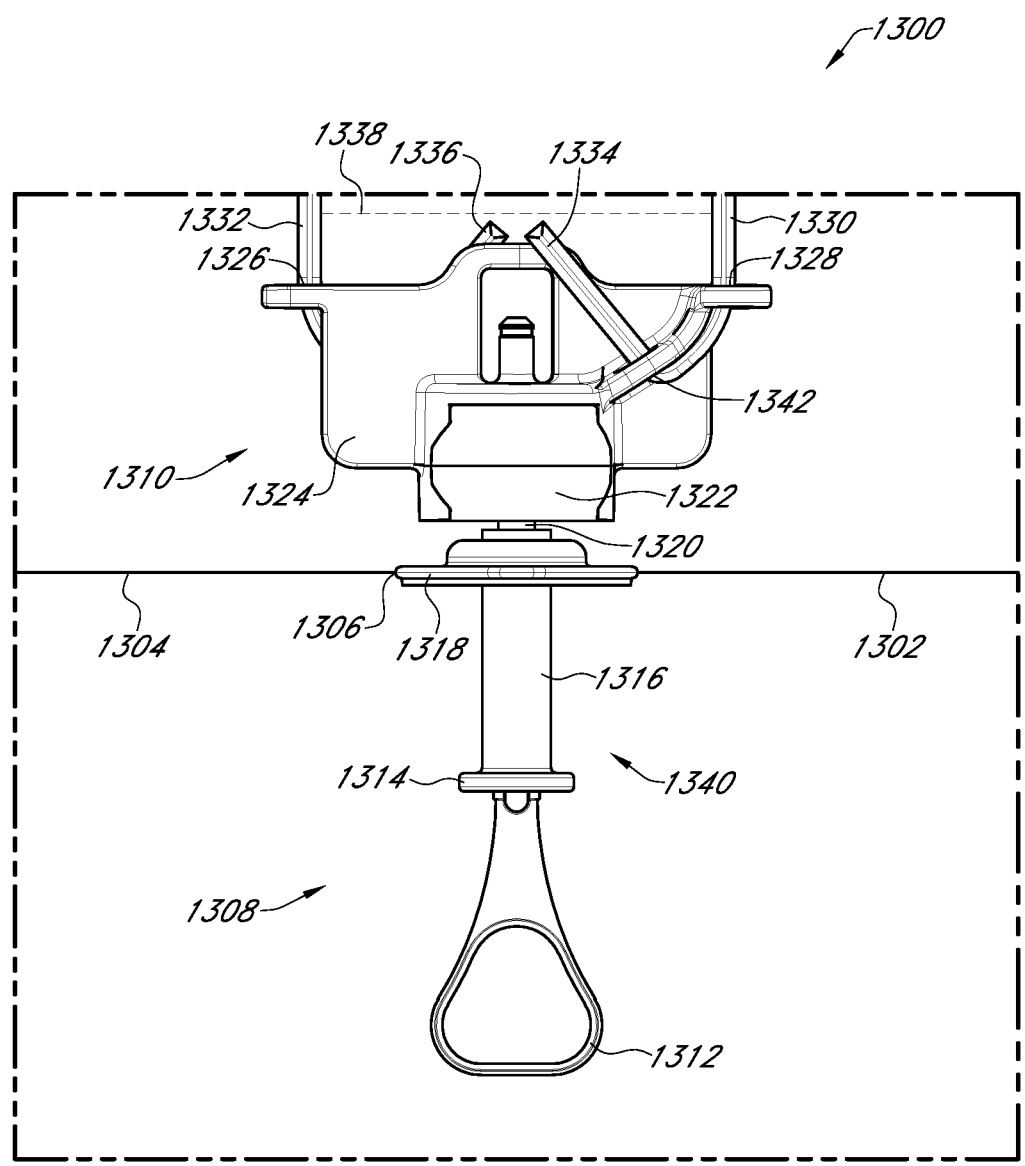
FIG. 13 illustrates a second bearing assembly and yoke/impeller 1300 in accordance with one embodiment.

FIG. 13 illustrates a second bearing assembly and yoke/impeller 1300 mounted to a flexible compartment 1302 according to various embodiments. The second bearing assembly and yoke/impeller 1300 may assemble onto the flexible compartment 1302 and the flexible compartment 1302 may include a second end 1304 with an opening 1306. The second end 1304 separates an exterior 1308 from an interior 1310 to maintain sterility on the interior 1310. A second bearing assembly may be mounted to the second end 1304 and may include a pull handle 1312, an attachment ring 1314, a retaining post 1316, a second annular sealing flange 1318, a thrust pin 1320, and a bearing cup 1322. The bearing cup 1322 may serve to mount to a yoke/impeller 1324 and the yoke/impeller 1324 may include one or more yoke/impeller openings 1326, 1328 and the yoke/impeller 1324 may serve to secure a first line 1330 and a second line 1332 by interacting with a first end 1334 and a second end 1336. The yoke/impeller 1324 may aid the yoke 814 to set a helical width 1338.

In various embodiments, the first line 1330 and the second line 1332 may be spaced apart by threading the first end 1334 and the second end 1336 through opposing yoke/impeller openings 1326, 1328 located on the yoke/impeller 1324 to create a helical width 1338. In various embodiments the first and second lines 1330, 1332 may then be secured to the yoke/impeller 1324 by threading the ends 1334, 1336 through securing holes 1342. Alternatively, the lines 1330, 1332 may be secured to the yoke/impeller 1324 by adhesion, welding or by the same hole and opening arrangement seen on the yoke 814 depicted in FIG. 8.

Figure 14:
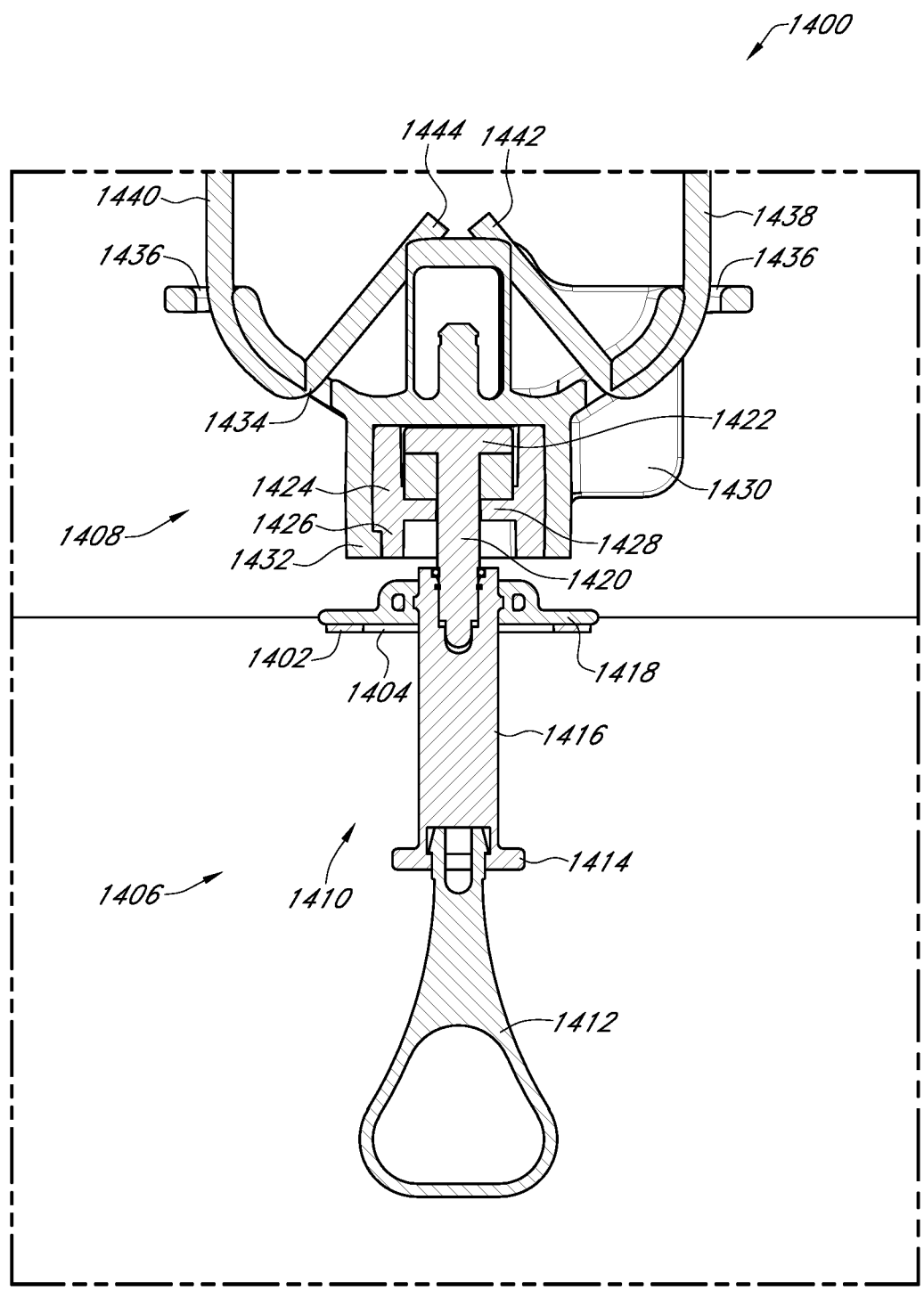
FIG. 14 illustrates a cross sectional view of a second bearing assembly and yoke/impeller 1400 in accordance with one embodiment.

FIG. 14 illustrates a cross sectional view of what is depicted in FIG. 13 according to various embodiments. The second bearing assembly and yoke/impeller 1400 may mount onto a flexible compartment 1402 through an opening 1404. The flexible compartment 1402 may include a second end 1444 separating an exterior 1406 and an interior 1408 to maintain sterility on the interior 1408. The second bearing assembly 1410 may include a pull handle 1412, an attachment ring 1414, a retaining post 1416, and a second annular sealing flange 1418 that can be adhered, welded, or joined any suitable manner to the perimeter of the opening 1404. The second bearing assembly 1410 may further include, a thrust pin 1420, a pin head 1422, a bearing cup 1424, a notch 1426, and a bearing cup flange 1428. A yoke/impeller 1430 can connect the bearing cup 1424 and may include a yoke/impeller flange 1432, securing holes 1434, and a yoke/impeller openings 1436. A first line 1438 and a second line 1440 may include a first end 1442 and a second end 1444, respectively, that can be threaded through the yoke/impeller openings 1436 and secured onto the securing holes 1434.

In various embodiments, the bearing cup 1424 may include a notch 1426 that is sized to allow the bearing cup 1424 to be retained within a yoke/impeller flange 1432. Alternatives to securing the bearing cup 1424 to the yoke/impeller 1430 may include adhering, welding or joining in a manner resilient to rotational movement.

Figure 15:
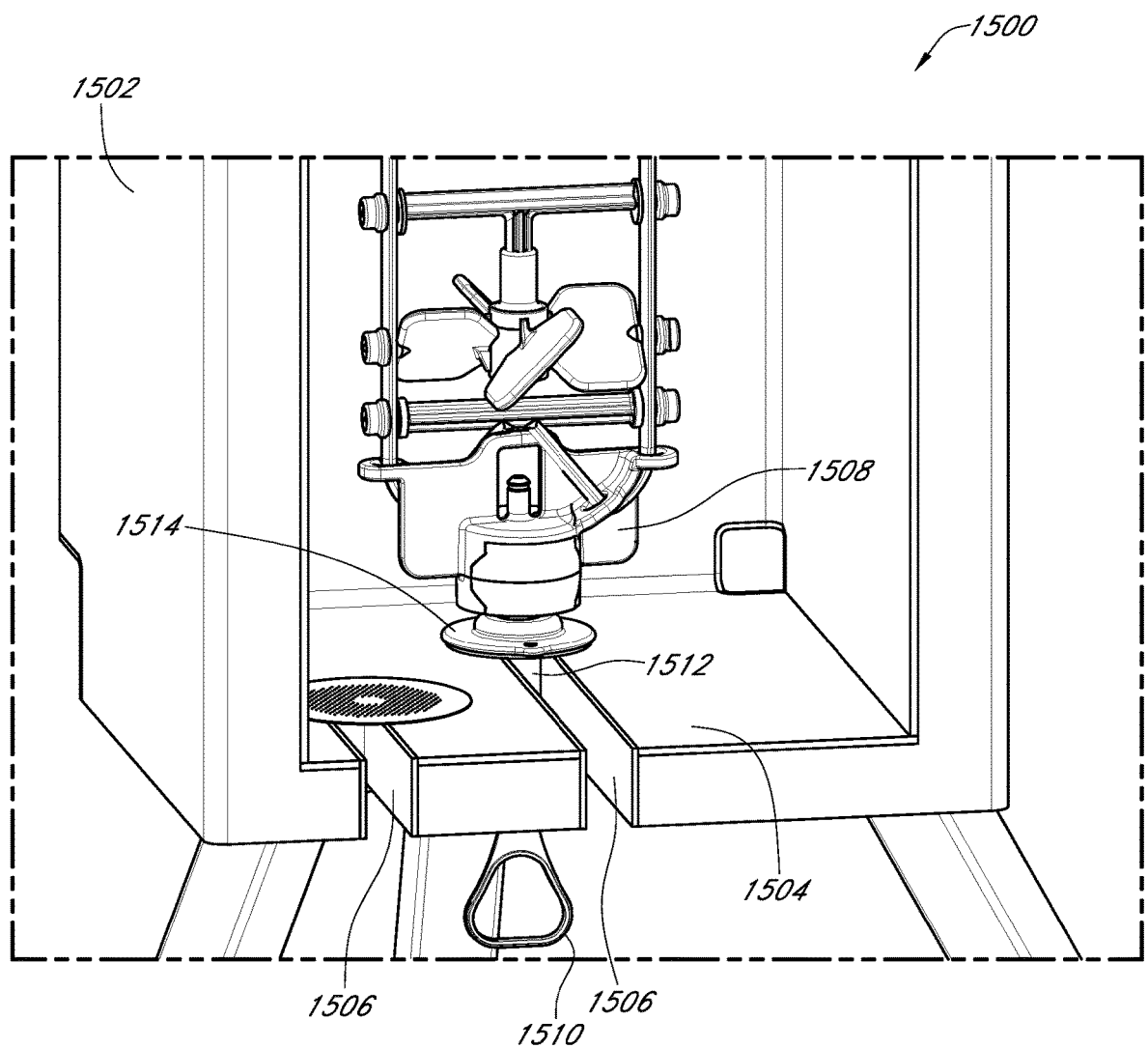
FIG. 15 illustrates a mixing system 1500 in accordance with one embodiment.
Figure 16:
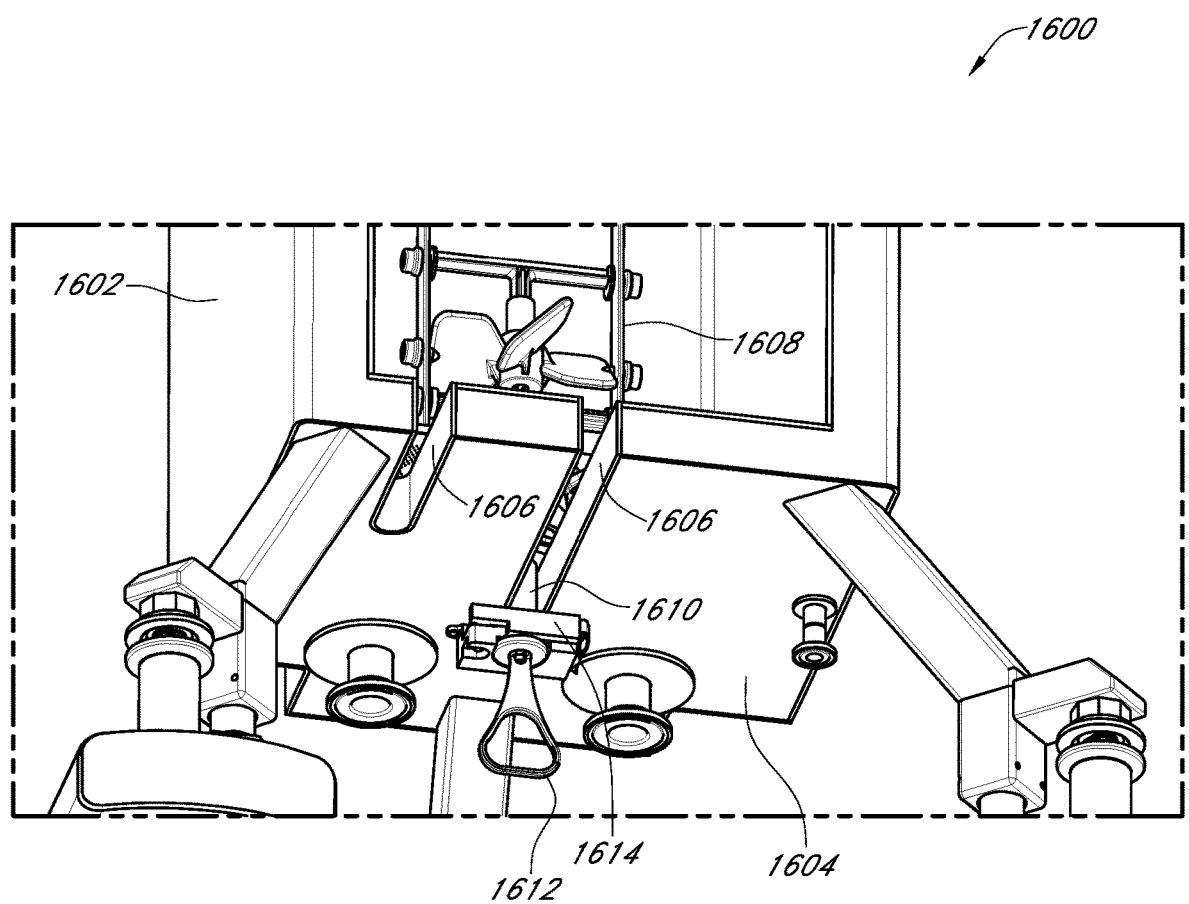
FIG. 16 illustrates a mixing system 1600 in accordance with one embodiment.

FIGS. 15 and 16 illustrate a mixing system 1500, 1600 according to various embodiments. The mixing system 1500, 1600 may comprise a rigid housing 1502, 1602 having a rigid housing floor 1504 and a floor exterior 1604 with one or more openings 1506, 1606 for insertion of a helical assembly 1508, 1608. The helical assembly 1508, 1608 may be pulled into place by a user adjusting a pull handle 1510, 1612 to move a helical assembly 1508 into a resting place within one of the openings 1506, 1606. The helical assembly 1508, 1608 may be secured by having a second annular sealing flange 1514 abut the rigid housing floor 1504 on one side and an assembly latch 1614 moveable from an open to a closed position abutting and securing the helical assembly 1508, 1608 on the floor exterior 1604.

Figure 17:
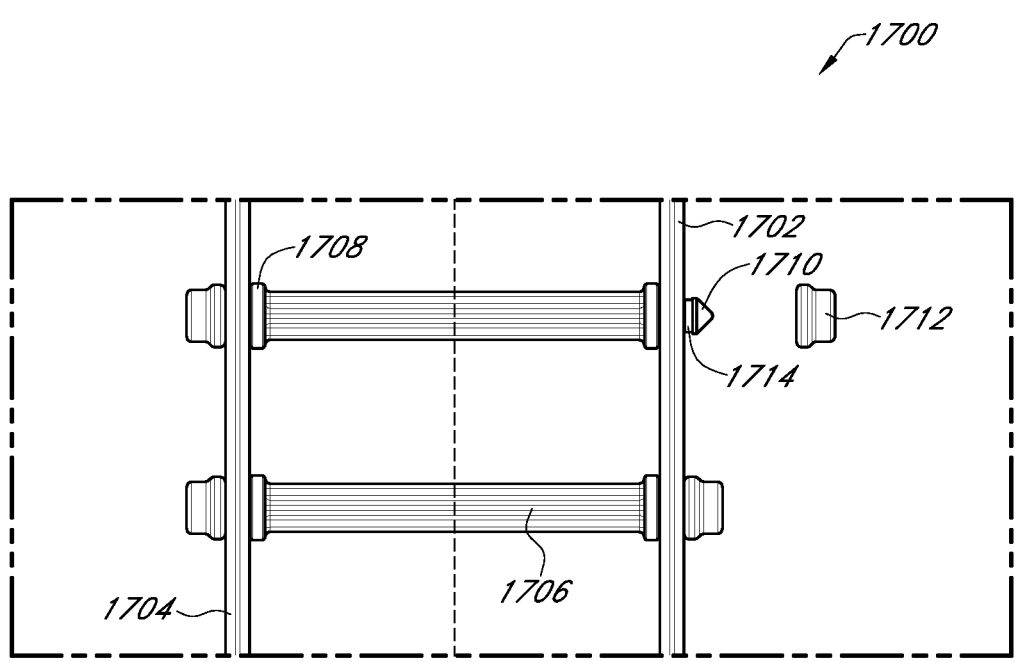
FIG. 17 illustrates a close up view of a portion of a helical assembly 1700 in accordance with one embodiment.

FIG. 17 illustrates a portion of a helical assembly 1700 according to various embodiments. The helical assembly 1700 may comprise a first line 1702 and a second line 1704 joined together by a rung 1706 wherein the rung 1706 includes two ends 1710, rung flanges 1708 adjacent to the ends 1710, and a rung cap 1712 may be used to secure each end 1710 of the rung 1706 to the lines 1702, 1704.

In various embodiments, the first line 1702 and the second line 1704 include a plurality of openings (shown in later figures) and a first end 1710 of a rung 1706 can be threaded through an opening on the first line 1702 until a rung flange 1708 abuts the first line 1702 and a second end 1710 of a rung 1706 can be threaded through an opening on the second line 1704 until a rung flange 1708 abuts the second line 1704. In some embodiments, rung caps 1712 may be used to secure the rung ends 1710 to the first and second lines 1702, 1704. In some embodiments, adhesive, welding, pins, knots, ties, or any other device or joining technique may be used to secure the rungs 1706 to the lines 1702, 1704.

In various embodiments, the rung ends 1710 may include a rung recess 1714 that allows a protrusion inside of the rung caps 1712 to snap into place.

In various embodiments, the lines 1702, 1704 may be produced from any kind of known thread or cord as well as polymers suitable to resist tensile stress.

In various embodiments, the lines and rungs may be made from rope, cord, plastic polymer, string, wire, or anything else known or useful. In some embodiments, the lines may be made from a flat plastic polymer and in some situations may be multilayered using the same or similar materials used in the flexible container. In various embodiments, the ends and caps can be made from plastic polymer, metal polymer, or anything else known or useful.

Figure 18:
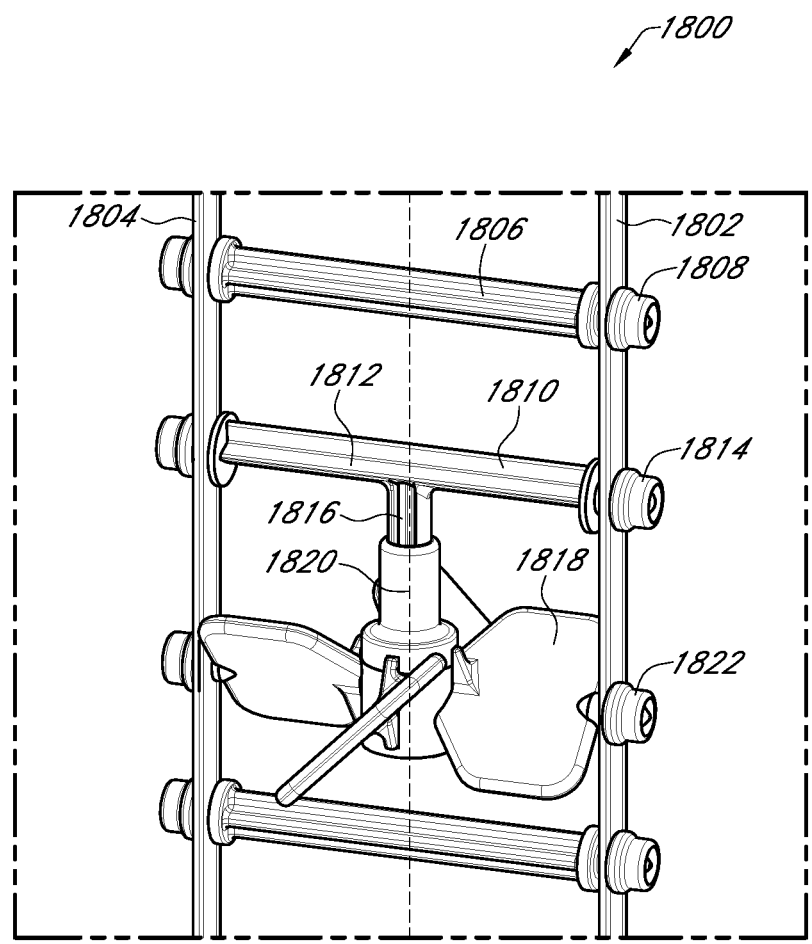
FIG. 18 illustrates a close up view of a portion of a helical assembly 1800 in accordance with one embodiment.

FIG. 18 illustrates a portion of a helical assembly 1800 according to various embodiments. The helical assembly 1800 may comprise a first line 1802 and a second line 1804 with rungs 1806, stabilizers 1810, and impellers 1818 attached thereto.

In various embodiments, a rung 1806 extends and connects between the two lines 1802,1804 to stabilize the helical structure both while idle and while in use. Rung caps 1808 may be used to secure the rungs 1806 to the lines 1802, 1804. In use the entire assembly may rotate very quickly and the rungs 1806 serve as both structural support elements as well as provide increased mixing. The number of rungs 1806 used for a given application may require optimization to reduce laminar fluid flow and maximize bulk fluid flow.

In various embodiments, a stabilizer 1810 may include a cross member 1812 where the cross member 1812 may include ends that secure to the first and second lines 1802, 1804 using two or more stabilizer caps 1814. In some embodiments the stabilizer 1810 may include a stem 1816 that projects toward an impeller 1818 adjacent to the stabilizer 1810.

In various embodiments, an impeller 1818 has two ends that extend and connect to the first and second lines 1802, 1804 with impeller caps. In general, caps or other securing means may hold various elements stationary relative to the first and second lines 1802, 1804. In some embodiments, the impeller 1818 may include a receiver 1820 that projects toward the stabilizer 1810/stem 1816. The stem 1816 may be received within the receiver 1820 to prevent the impeller 1818 from flipping along its end to end axis. Without an interaction between the stabilizer 1810 and impeller 1818 the impeller 1818 will flip to an orientation that provides the least resistance. Such an orientation, in most cases, would not be optimal for bulk fluid flow.

In various embodiments, the stem 1816 can move in and out of the receiver 1820 to accommodate varying rotational speeds of the helical assembly 1800. In some embodiments, the stabilizer 1810 stem 1816 can be fixed by weld, adhesive, or be integral with the impeller 1818. In such an embodiment, the first and second lines 1802, 1804 may be able to slide relative to the cross member 1812 ends.

In various embodiments, an interaction between a stabilizer 1810 and impeller 1818 parts can resemble anything that would allow for the stabilizer 1810 to assist the impeller 1818 in maintaining a stable planar orientation. In some embodiments, the impeller 1818 may include a stem 1816 and the stabilizer 1810 may include a receiver 1820. In some embodiments, an impeller 1818 may have two or more locations of attachment to each line 1802, 1804. In some such an embodiment, one attachment may be fixed and one attachment may slide to accommodate the twisting of the lines 1802, 1804 as the helical assembly 1800 is in use.

Figure 19:
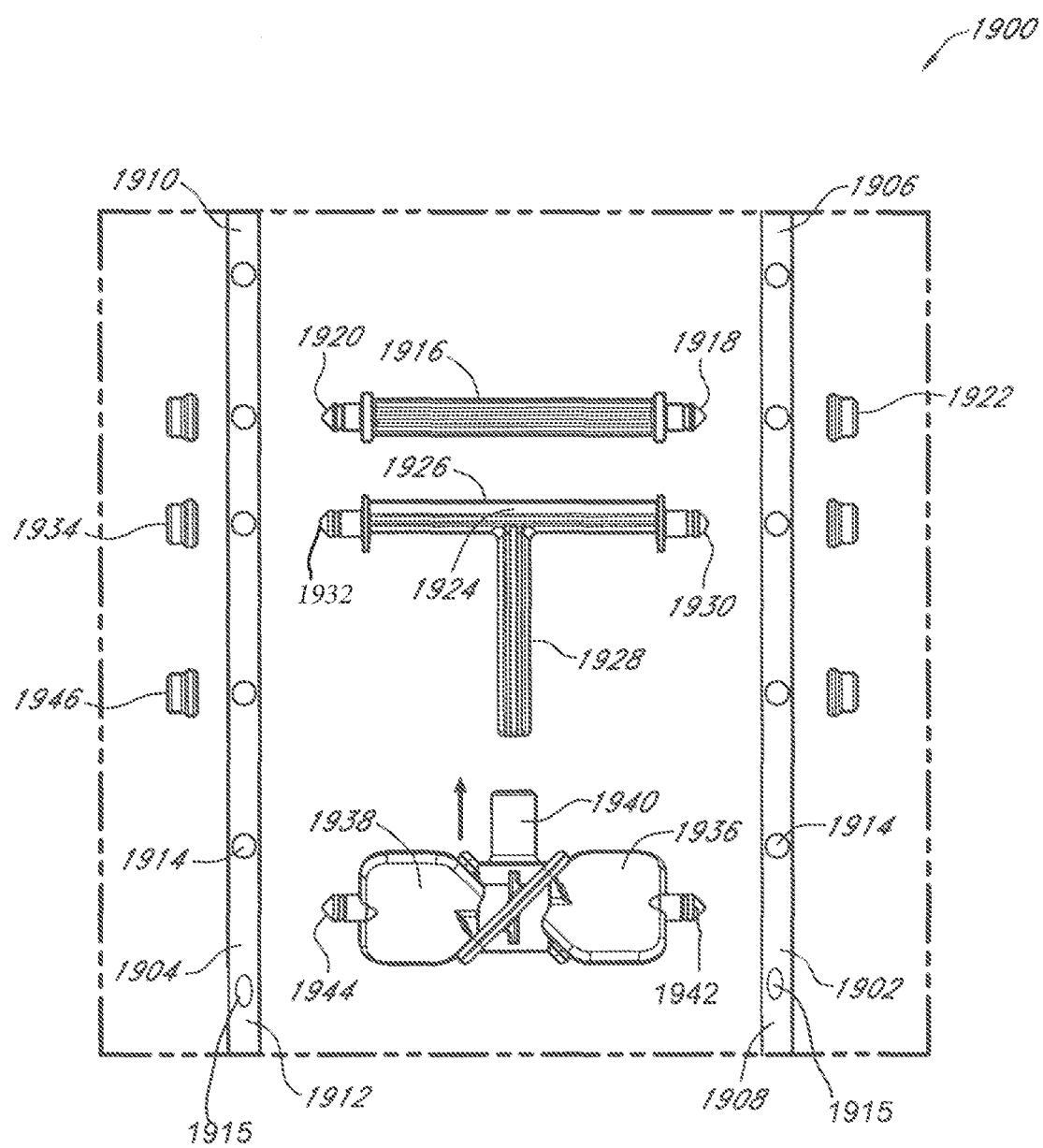
FIG. 19 illustrates an exploded view of a helical assembly 1900 in accordance with one embodiment.

FIG. 19 is an illustration of an exploded view of a portion of a helical assembly 1900 according to various embodiments. The helical assembly 1900 may comprise a first line 1902, a second first line 1902, one or more rungs 1916, one or more stabilizers 1924, and one or more impellers 1936. First line 1902 extends between an upper end 1906 and an opposing lower end 1908 while second line 1904 extends between an upper end 1910 and an opposing lower end 1912.

In various embodiments, the helical assembly may comprise one or more rungs 1916 having a first protrusion 1918 that projects through an opening 1914 on a first line 1902 and a second protrusion 1920 that projects through an opening 1914 on a second line. In some embodiments, run caps 1922 may snap onto the protrusions to secure the rungs 1916 to the lines.

In various embodiments, the helical assembly 1900 may include a stabilizer that includes a crossmember 1926 having a first end 1930 that projects through an opening 1914 on the first line 1902 and a second end 1932 that projects through an opening 1914 on the second line 1904. Stabilizer caps 1934 may snap onto the ends 1930, 1932 to secure the stabilizer onto the helical assembly 1900. In some embodiments, a stem 1928 may project from the center and perpendicular to the crossmember 1926.

In various embodiments, an impeller 1936 may include a crossmember 1938 having a first attachment 1942 that projects through an opening 1914 on the first line 1902 and a second attachment 1944 that projects through an opening 1914 on the second line 1904. In various embodiments, a receiver 1940 may extend from the center and perpendicular to the crossmember 1938.

In various embodiments, the receiver 1940 may be tubular in nature and accept a stem 1928 from the stabilizer 1924. The receiver 1940 and stem 1928 may slide relative to one another as the rotational rate of the helical assembly 1900 varies. In some embodiments, openings 1914 on lines 1902 and 1904 that receive first and second attachments 1942 and 1944 can comprise oval shaped opening 1915 that allow movement of first and second attachments 1942 and 1944 along the length of the lines 1902 and 1904.

Figure 20:
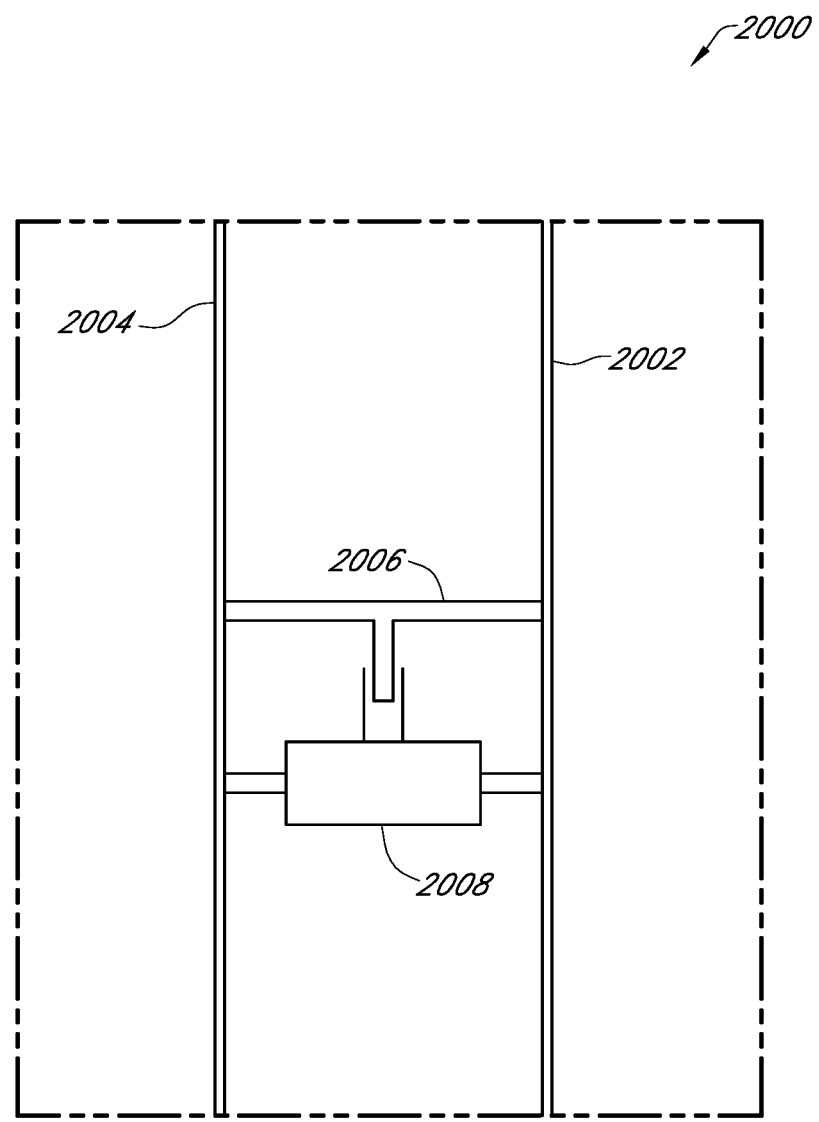
FIG. 20 illustrates a helical assembly 2000 in accordance with one embodiment.

FIG. 20 illustrates a portion of a helical assembly 2000 in an untwisted planar position according to various embodiments. The helical assembly 2000 may comprise a first line 2002 and a second line 2004 in a parallel configuration relative to one another. A stabilizer 2006 and an impeller 2008 are in a second position 2300 relative to one another. Such a configuration is likely to occur when the mixing system is not in use.

Figure 21:
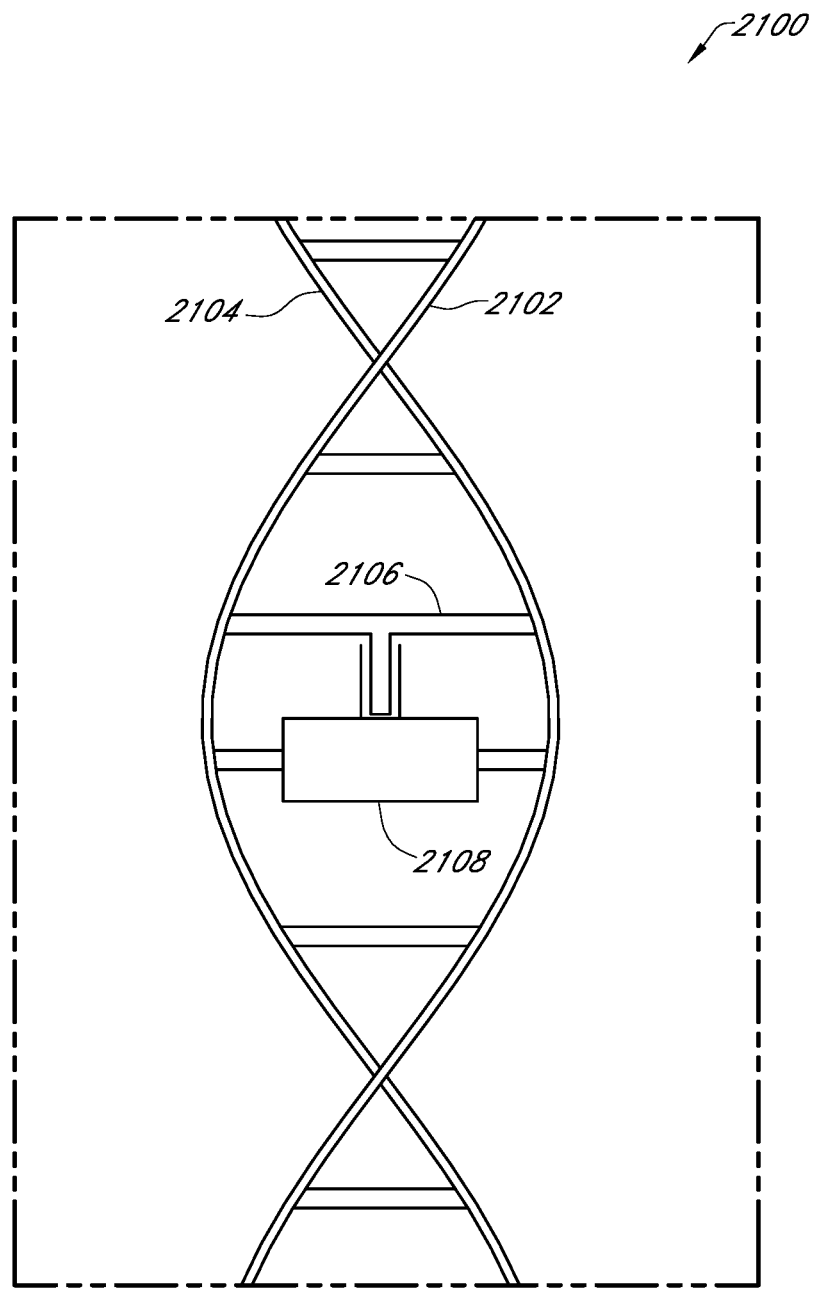
FIG. 21 illustrates a helical assembly 2100 in accordance with one embodiment.

FIG. 21 illustrates a portion of a helical assembly 2100 in a twisted configuration according to various embodiments. The helical assembly 2100 may comprise a first line 2102 and a second line 2104, wrapped about a driveline axis 738 (FIG. 7) and twisted about one another. A stabilizer 2106 and an impeller 2108 are in a first position relative to one another.

Figure 22:
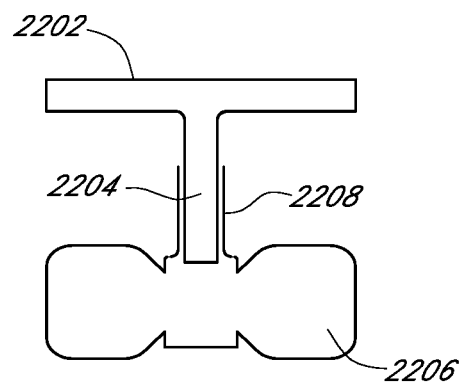
FIG. 22 illustrates a first position in accordance with one embodiment.

FIG. 22 illustrates a stabilizer 2202 and an impeller 2206 in a first position relative to one another according to various embodiments. The stabilizer 2202 may include a stem 2204 and the impeller 2206 may include a receiver 2208. In some embodiments the first position may include the stem 2204 extending further into the receiver 2208 than in a second position. In some embodiments the first position may include the stem 2204 not extending further into the receiver 2208 than when in the second position. In some embodiments, the first position and the second position may include the stem 2204 and receiver 2208 being in the same position.

Figure 23:
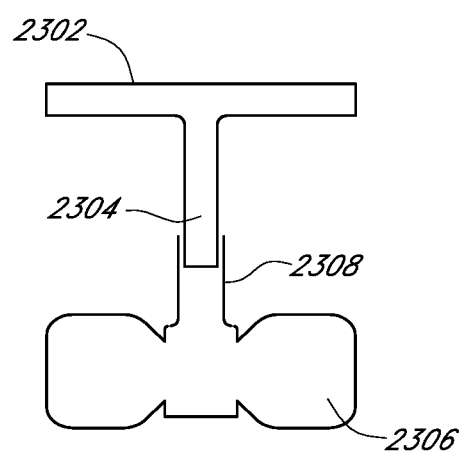
FIG. 23 illustrates a second position in accordance with one embodiment.

FIG. 23 illustrates a stabilizer 2302 and an impeller 2306 in a second position relative to one another according to various embodiments. The stabilizer 2302 may include a stem 2304 and the impeller 2306 may include a receiver 2308. In some embodiments the second position may include the stem 2304 extending further into the receiver 2308 than in a second first position. In some embodiments the second position may include the stem 2304 not extending further into the receiver 2308 than when in the first position. In some embodiments, the first position and the second position may include the stem 2304 and receiver 2308 being in the same position.

Figure 24:
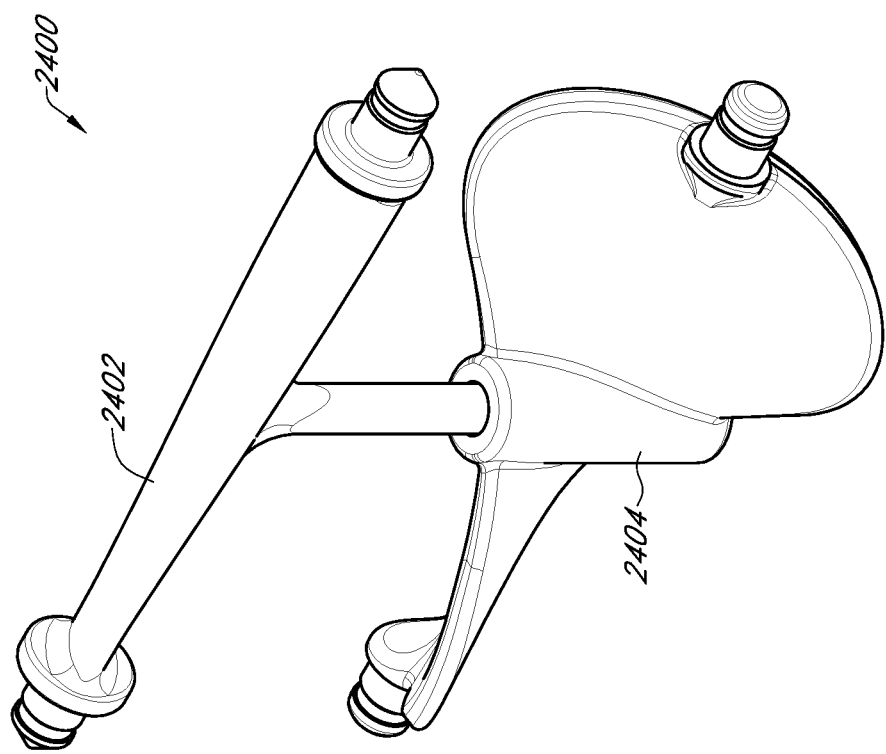
FIG. 24 illustrates a stabilizer/impeller 2400 in accordance with one embodiment.
Figure 25:
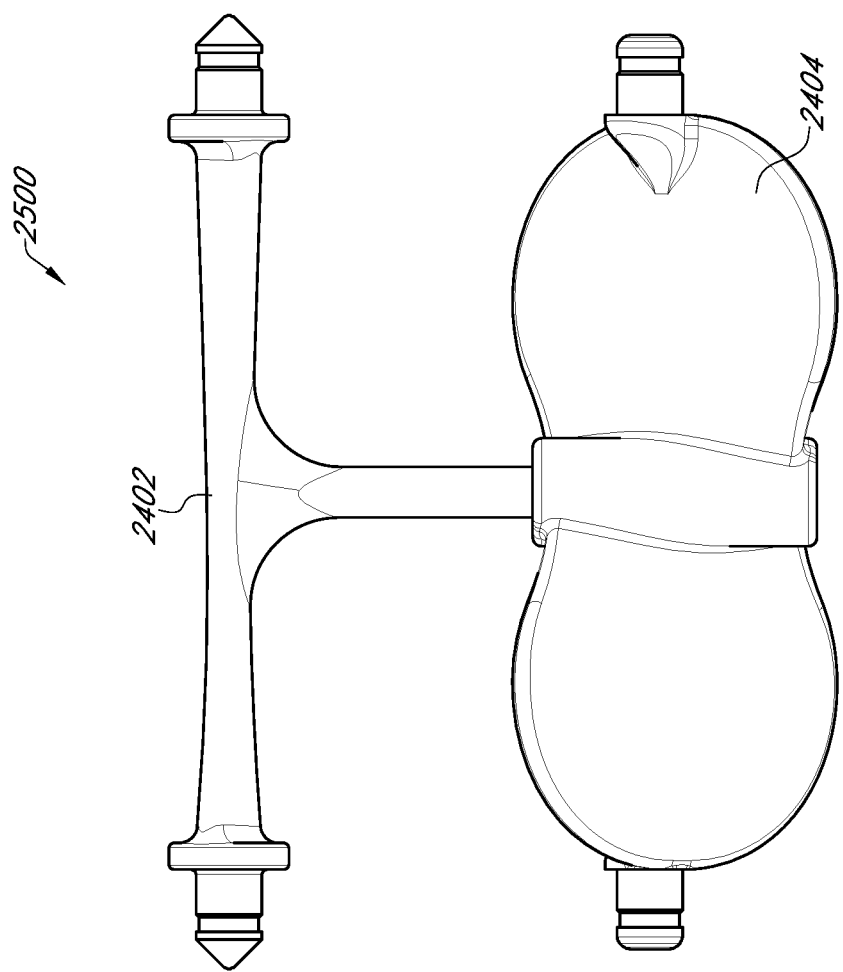
FIG. 25 illustrates a stabilizer/impeller 2500 in accordance with one embodiment.

FIGS. 24 and 25 are illustrations of different views of an example of a stabilizer/impeller 2400, 2500 according to various embodiments. The stabilizer/impeller 2400/2500 comprises a stabilizer 2402 and an impeller 2404.

Figure 26:
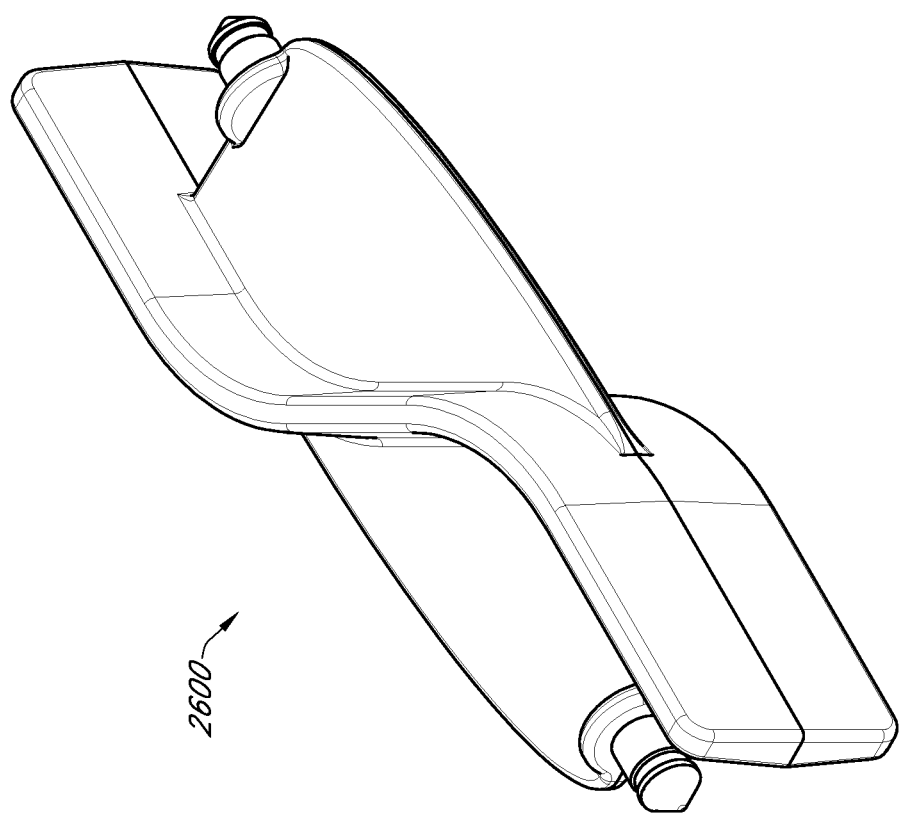
FIG. 26 illustrates a rung impeller 2600 in accordance with one embodiment.

FIG. 26 is an illustration of a rung impeller 2600 according to various embodiments. In some embodiments, a rung impeller 2600 does not require a stabilizer 746 (FIG. 7) for proper orientation because the symmetry of the rung impeller 2600 causes it to self-orient.

Figure 27:
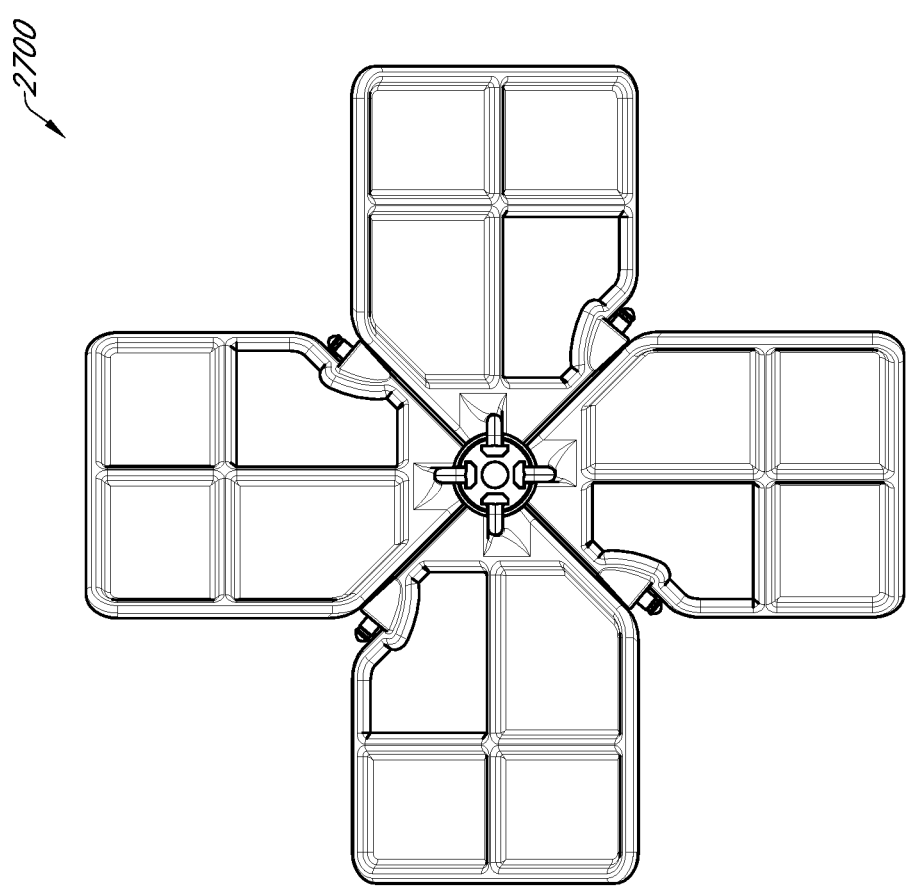
FIG. 27 illustrates an impeller 2700 from a top down view in accordance with one embodiment.

FIG. 27 is a top down view of an impeller 2700 according to various embodiments.

Figure 28:
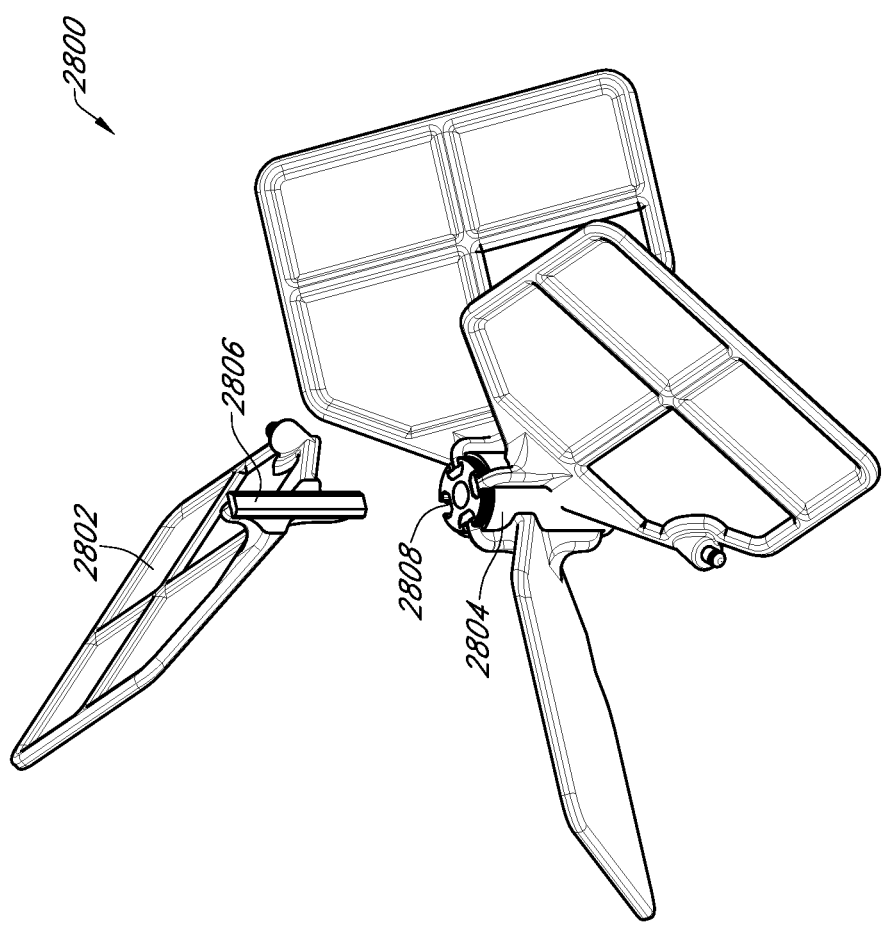
FIG. 28 illustrates an impeller 2800 and fin 2802 attachment accordance with one embodiment.

FIG. 28 is an illustration of one possible way the fins 2802 of an impeller 2800 can attach to a central hub 2804. In some embodiments, a fin 2802 may include a member 2806 that is designed to slide into a groove 2808 on the central hub 2804 and be retained through frictional force. In some embodiments, the impeller 2700, 2400, 2500, 2800 may be molded into a single piece.

Figure 29:
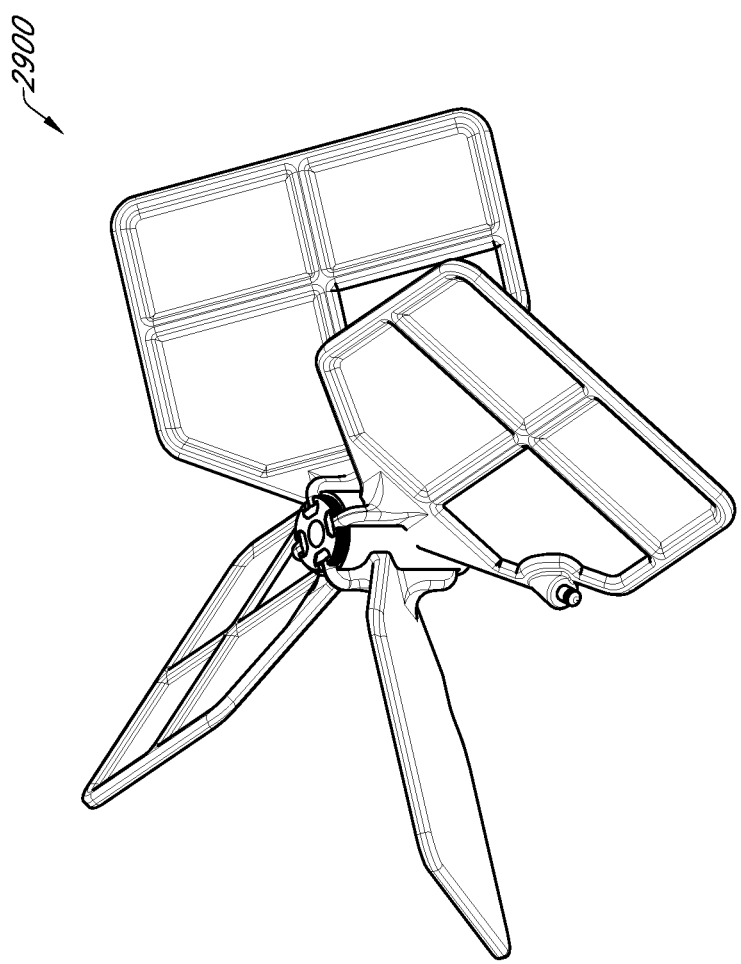
FIG. 29 illustrates an impeller 2900 with fin orientation in accordance with one embodiment.

FIG. 29 is an illustration of an impeller 2900 to show one possible orientation for the fins 2802 (FIG. 28).

Figure 30:
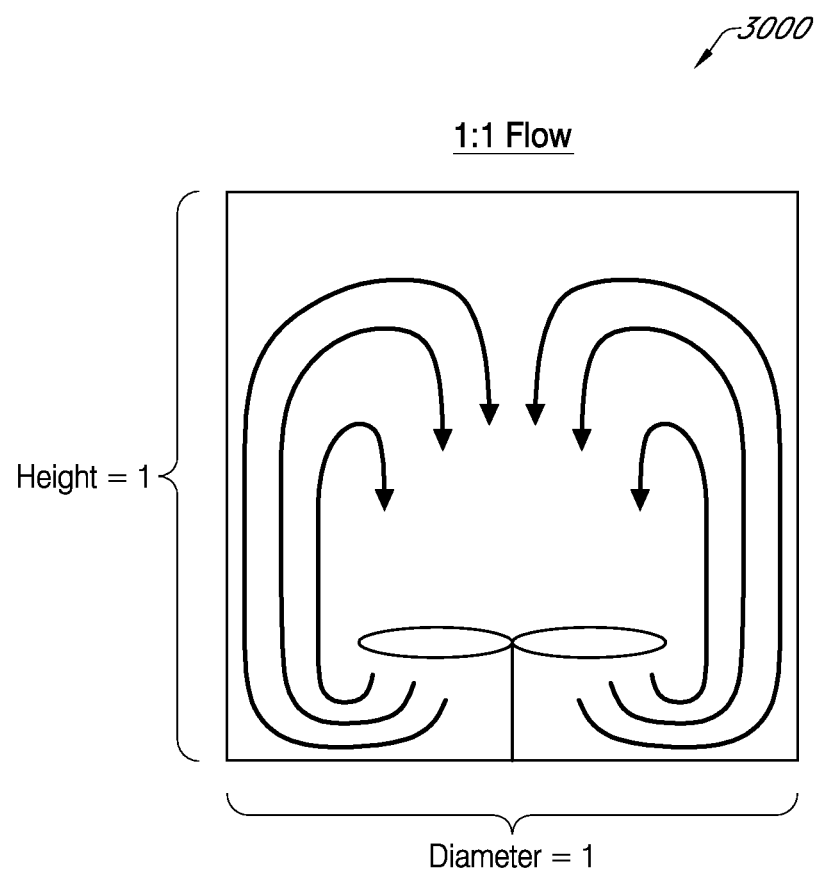
FIG. 30 illustrates a mixing system 3000 in accordance with the prior art.

FIG. 30 illustrates a mixing system 3000 according to the prior art. This particular mixing system 3000 is cylindrical with a drive shaft and impeller located in the center of the tank. The arrows show how fluid flows in such a system with the impeller in operation.

Figure 31:
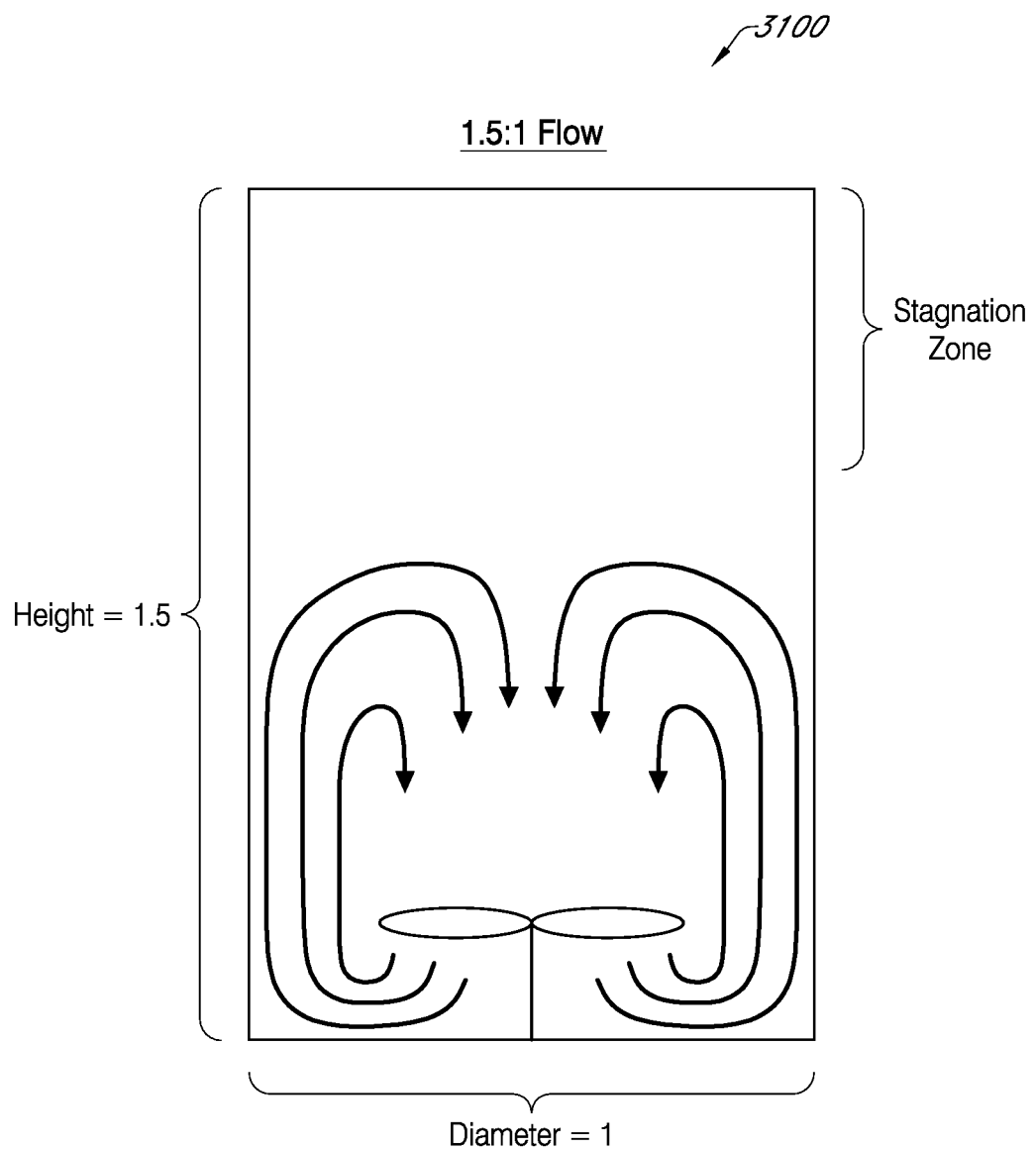
FIG. 31 illustrates a mixing system 3100 in accordance with the prior art.

FIG. 31 illustrates a mixing system 3100 according to the prior art. This particular mixing system 3100 has a larger height than diameter, but is otherwise very similar to the mixing system 3000 depicted in FIG. 30. Such a mixing system 3100 has scalability problems because stagnation zones begin to appear where fluid is not being mixed properly.

Figure 32:
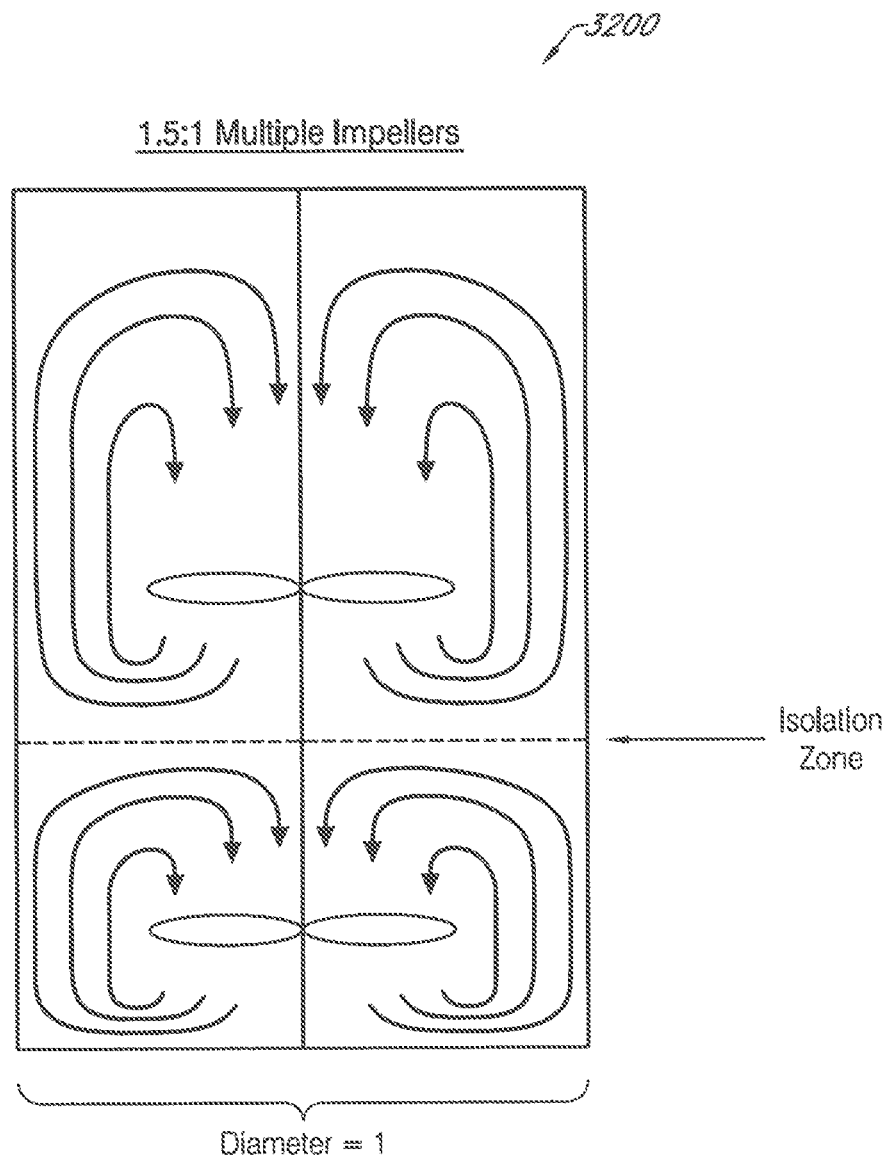
FIG. 32 illustrates a mixing system 3200 that is one possible solution to the prior art.

FIG. 32 illustrates a mixing system 3200 including a driveshaft extending from the bottom to the top of the tank with impellers centered within the tank. Such a design resolves some of the issue relating to stagnation zones seen in FIG. 31, however, due to the driveshaft and impellers being centered within the tank an isolation zone has appeared. This means that a top layer and a bottom layer form and they fail to intermix efficiently.

Figure 33:
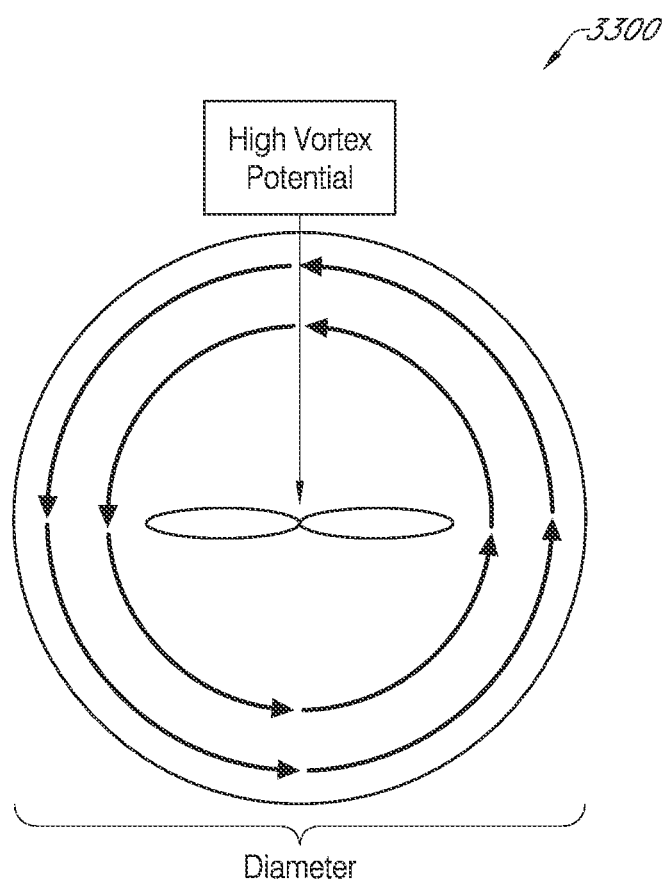
FIG. 33 illustrates a mixing system 3300 showing a vortex that may occur in prior art mixing systems.

FIG. 33 illustrates problems that may occur in the mixing systems 3000, 3100, and 3200 depicted in FIGS. 30-32. Specifically, centered impellers without some kind of physical baffling device have the potential to create a vortex in the fluid. The problem with vortexes is that the materials in the fluid move relative to one another which reduces mixing efficiency.

FIG. 34 illustrates a mixing system 3400 in accordance with the various embodiments. The mixing system 3400 shown in FIG. 34 includes a rectangular shape.

Figure 35:
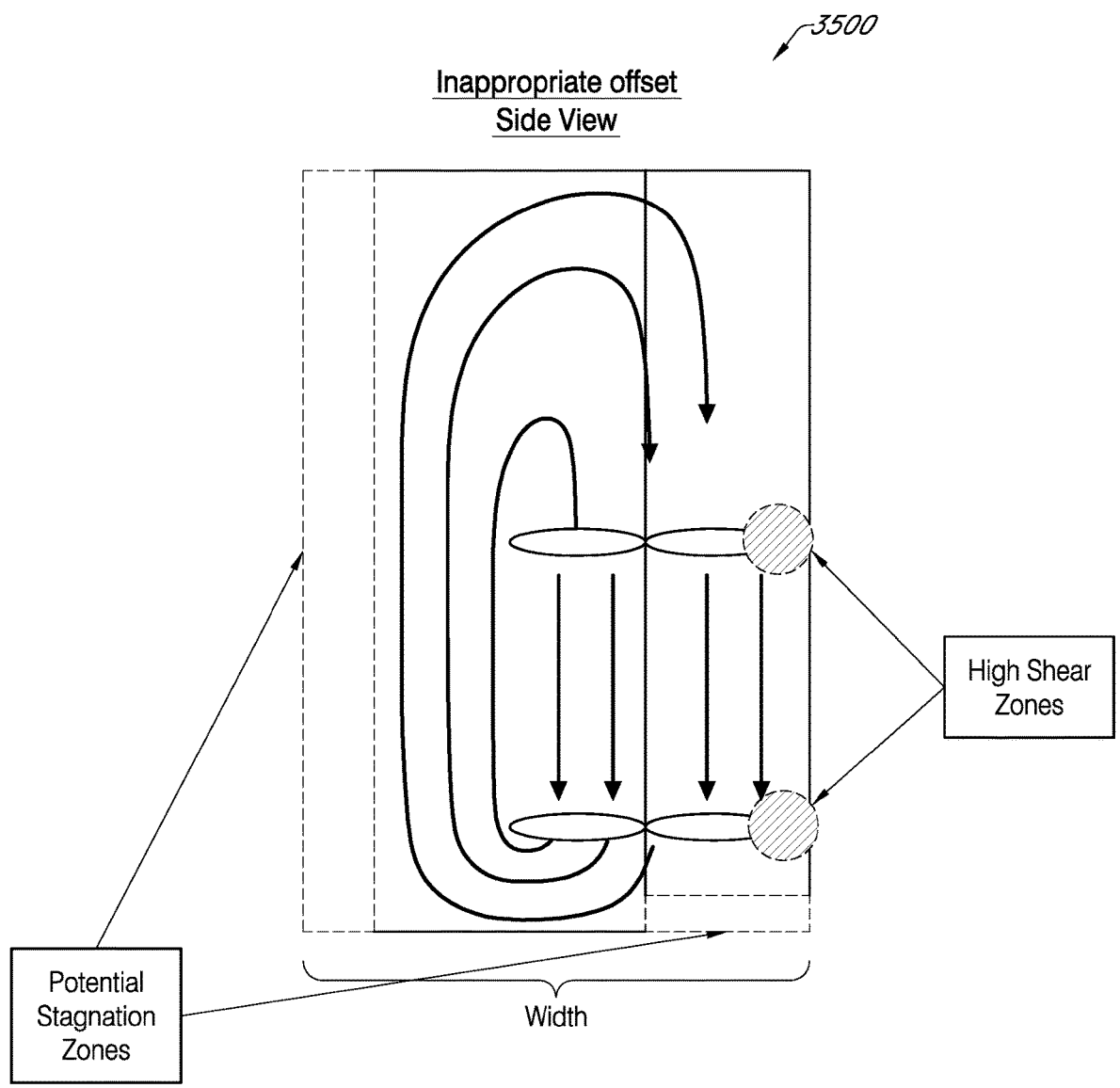
FIG. 35 illustrates a mixing system 3500 including an inappropriately offset drive assembly.

FIG. 35 illustrates a mixing system 3500 having an inappropriate offset for a drive assembly that is causing stagnation zones where mixing is ineffective and high shear zones which have the potential to damage the cells or material being mixed.

Figure 36:
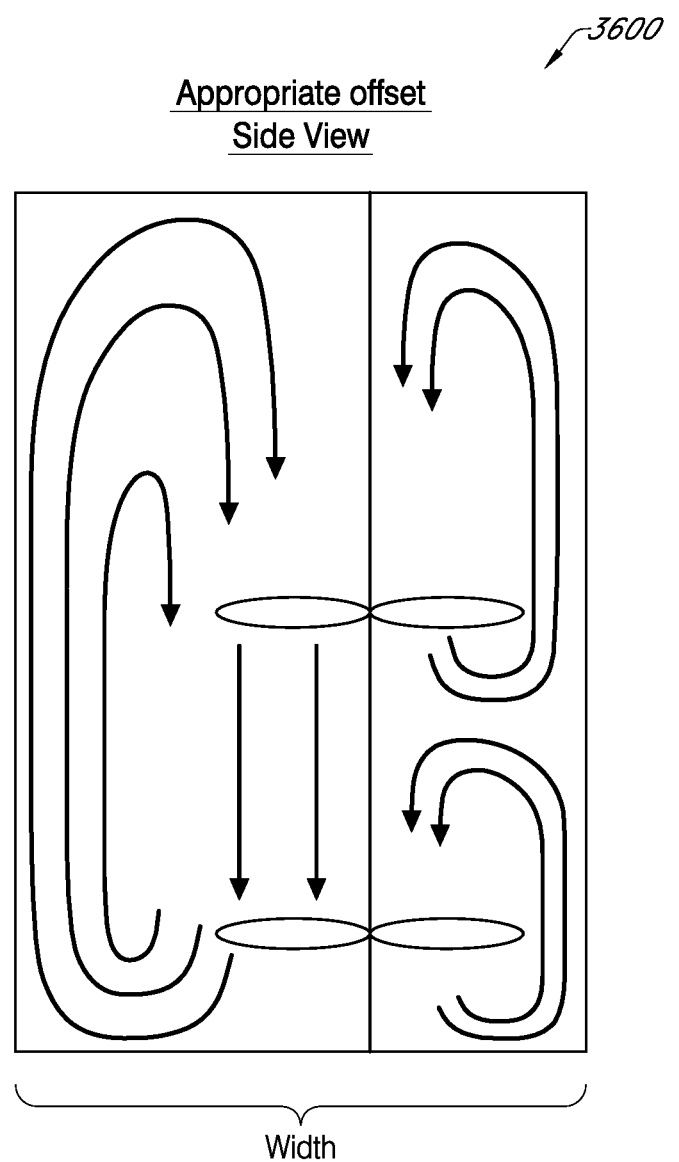
FIG. 36 illustrates a mixing system 3600 including an appropriately offset drive assembly.

FIG. 36 illustrates a mixing system 3600 having an optimized offset location for a drive assembly that maximizes bulk fluid flow while minimizing or eliminating stagnation zones, isolation zones, and high shear zones.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequences may be varied and still remain within the spirit and scope of the various embodiments.

What is claimed is:

1. A bioproduction mixing assembly, comprising:
a first line and a second line;
a stabilizer including a cross member having a first end and a second end with a first portion disposed on the cross member, the first portion comprising a stem or a tubular receiver, wherein the first end of the cross member engages the first line and the second end of the cross member engages the second line;
an impeller including a second portion, a first attachment, and a second attachment,
wherein the first attachment engages the first line and the second attachment engages the second line, the second portion comprising the other of the stem or the tubular receiver, the stem being received within the tubular receiver.

2. The bioproduction mixing assembly of claim 1, wherein the first and second lines each include a plurality of openings and the first end of the cross member projects into a first opening on the first line and the second end of the cross member projects into a first opening on the second line.

3. The bioproduction mixing assembly of claim 2, wherein the first attachment projects into an opening on the first line and the second attachment projects into an opening on the second line.

4. The bioproduction mixing assembly of claim 2, wherein stabilizer caps affix to the first end and the second end of the cross member to secure the stabilizer to the first and second lines.

5. The bioproduction mixing assembly of claim 3, wherein impeller caps affix to the first and second attachments to secure the impeller to the first and second lines.

6. The bioproduction mixing assembly of claim 1, further comprising a plurality of rungs, wherein each rung has a first protrusion projecting into an opening on the first line and a second protrusion projecting into an opening on the second line, wherein the protrusions affix to rung caps to secure the rungs to the lines.

7. The bioproduction mixing assembly of claim 1, further comprising a flexible container having a first end and a second end joined together by a sidewall, wherein the first and second lines are each suspended between the first and second ends of the flexible container and the first and second lines are spaced apart and on opposing sides of a driveline axis.

8. The bioproduction mixing assembly of claim 7, wherein a first bearing assembly is mounted to the first end of the flexible container and a second bearing assembly is mounted to the second end of the flexible container to provide rotational movement to the first line and second line.

9. The bioproduction mixing assembly of claim 8, wherein the flexible container further comprises
an inlet for introducing a fluid into the flexible compartment;
an outlet for removing a fluid from the flexible compartment;
at least one sensor port for receiving a sensor; and
a sparger for introducing a gas into the flexible compartment.

10. The bioproduction mixing assembly of claim 9, further comprising a rigid housing adapted to receive the flexible container, wherein the rigid housing includes a rigid housing support and a motor configured to engage the first bearing assembly and provide rotational energy to the first line and second line.

11. The bioproduction mixing assembly of claim 1, wherein the first line and second line each comprise rope, cord, or wire.

12. The bioproduction mixing assembly of claim 1, wherein the first line and second line each comprise an elongated section of flat plastic polymer.

13. The bioproduction mixing assembly of claim 1, wherein the stem is slidable within the tubular receiver.

14. A bioproduction mixing assembly, comprising:
a flexible container having a first end and a second end joined together by a sidewall, the flexible container being comprised of one or more sheets of polymeric film;
a first line and a second line rotatably disposed within the flexible container; and
an impeller having a first end with first and second attachment positions and a second end with first and second attachment positions;
wherein the first attachment position of the first end is affixed to the first line and the first attachment position of the second end is affixed to the second line;
wherein the second attachment position of the first end is secured to the first line and the second attachment position of the second end is secured to the second line, the second attachment positions configured to slide along the lines while the mixing assembly is in operation.

15. The bioproduction mixing assembly of claim 14, wherein the attachment positions are protrusions that engage a set of openings in the first and second lines and the openings for receiving the second attachment positions are oval shaped to allow movement of the protrusions along the length of the lines.

16. The bioproduction mixing assembly of claim 14, wherein the first line and second line each comprise rope, cord, or wire or an elongated section of flat plastic polymer.

17. A bioproduction mixing assembly, comprising:
a flexible container having a first end and a second end joined together by a sidewall;
a first line and a second line disposed within the flexible container and being suspended between the first end and the second end thereof, the first line and the second line being rotatable relative to the flexible container;
a stabilizer including a cross member having a first end and a second end with a first portion disposed on the cross member, the first end of the cross member engaging the first line and the second end of the cross member engaging the second line; and
an impeller including a second portion, a first attachment, and a second attachment, the first attachment engaging the first line and the second attachment engaging the second line, the second portion engaging the first portion.

18. The bioproduction mixing assembly of claim 17, wherein a first bearing assembly is mounted to the first end of the flexible container and a second bearing assembly is mounted to the second end of the flexible container to provide rotational movement to the first line and the second line.

19. The bioproduction mixing assembly of claim 17, wherein the first line and second line each comprise rope, cord, or wire or an elongated section of flat plastic polymer.

20. The bioproduction mixing assembly of claim 17, wherein the flexible container is comprised of one or more sheets of polymeric film.

\* \* \* \* \*